(12) United States Patent
Vogt et al.

(10) Patent No.: US 11,389,599 B2
(45) Date of Patent: Jul. 19, 2022

(54) DISPLACEMENT DEVICE, TESTING DEVICE AND METHOD FOR LEAKAGE TESTING OF A CONNECTION OF A TIP CAP WITH A SYRINGE

(71) Applicant: Lonza Ltd, Visp (CH)

(72) Inventors: Martin Vogt, Allschwil (CH); Roman Mathaes, Basel (CH); Sarah Pelaez, Basel (CH); Anja Matter, Sissach (CH); Atanas Koulov, Basel (CH); Hanns-Christian Mahler, Loerrach (DE)

(73) Assignee: Lonza Ltd, Visp (CH)

( * ) Notice: Subject to any disclaimer, the term of this patent is extended or adjusted under 35 U.S.C. 154(b) by 0 days.

(21) Appl. No.: 17/429,959

(22) PCT Filed: Feb. 7, 2020

(86) PCT No.: PCT/EP2020/053188
§ 371 (c)(1),
(2) Date: Aug. 11, 2021

(87) PCT Pub. No.: WO2020/165052
PCT Pub. Date: Aug. 20, 2020

(65) Prior Publication Data
US 2022/0040416 A1    Feb. 10, 2022

Related U.S. Application Data

(60) Provisional application No. 62/804,355, filed on Feb. 12, 2019.

(30) Foreign Application Priority Data

Feb. 12, 2019 (EP) .................................... 19156785
Oct. 8, 2019 (EP) .................................... 19201988

(51) Int. Cl.
*A61M 5/34* (2006.01)
*A61M 5/32* (2006.01)
*G01M 3/04* (2006.01)

(52) U.S. Cl.
CPC .......... *A61M 5/344* (2013.01); *A61M 5/3202* (2013.01); *G01M 3/04* (2013.01); *A61M 2205/15* (2013.01); *A61M 2209/02* (2013.01)

(58) Field of Classification Search
CPC ... A61M 5/14546; A61M 2005/14553; G01M 3/02; G01M 3/202; G01M 3/226; G01M 3/229
See application file for complete search history.

(56) References Cited

U.S. PATENT DOCUMENTS 2,734,504 A * 2/1956 Crescas .................... A61M 5/20
604/155
3,701,345 A * 10/1972 Heilman ........... A61M 5/14546
600/432

(Continued)

FOREIGN PATENT DOCUMENTS

| DE | 3044550 A1 | 6/1982 |
| EP | 2 826 508 A1 | 1/2015 |

(Continued)

OTHER PUBLICATIONS

International Search Report and Written Opinion for PCT/EP2020/053188 dated Jul. 2, 2020, 15 pages.

*Primary Examiner* — Laura A Bouchelle
(74) *Attorney, Agent, or Firm* — Dority & Manning, P.A.

(57) ABSTRACT

The present invention relates to a displacement device, DD, for providing a displacement of a syringe closure system for a syringe relative to the syringe, a testing device, TD, and a method for leakage testing of a connection of a syringe closure system for a syringe with the syringe.

29 Claims, 15 Drawing Sheets

(56) References Cited

U.S. PATENT DOCUMENTS

| | | | |
|---|---|---|---|
| 9,074,960 B2 * | 7/2015 | Bonfiglioli | G01M 3/02 |
| 9,458,536 B2 | 10/2016 | Felts et al. | |
| 2013/0041241 A1 | 2/2013 | Felts et al. | |

FOREIGN PATENT DOCUMENTS

| WO | WO 2008/012611 A2 | 1/2008 |
|---|---|---|
| WO | WO 2012/103140 A1 | 8/2012 |
| WO | WO 2014/045336 A1 | 3/2014 |

* cited by examiner

US 11,389,599 B2

DISPLACEMENT DEVICE, TESTING DEVICE AND METHOD FOR LEAKAGE TESTING OF A CONNECTION OF A TIP CAP WITH A SYRINGE

CROSS REFERENCE TO RELATED APPLICATIONS

This application is the U.S. National Stage entry of International Application Number PCT/EP2020/053188 filed under the Patent Cooperation Treaty having a filing date of Feb. 7, 2020, which claims priority to U.S. Provisional Patent Application No. 62/804,355 having a filing date of Feb. 12, 2019, European Patent Application No. 19156785.8 having a filing date of Feb. 12, 2019, and European Patent Application No. 19201988.3 having a filing date of Oct. 8, 2019 which are incorporated herein by reference.

FIELD OF THE INVENTION

The present invention belongs to the field of container closure integrity, CCI, and testing of CCI and relates to a displacement device, DD, for providing a displacement of a syringe closure system for a syringe relative to the syringe, a testing device, TD, and a method for leakage testing of a connection of a syringe closure system for a syringe with the syringe.

TECHNOLOGICAL BACKGROUND

Pre-filled syringes, PFS, receive increasing attention as primary packaging and administration systems of choice for injectable drug products. This is due to several benefits PFS offer over the conventional glass vial, rubber stopper and crimp cap primary packaging combination. For example, PFS can add to a point of care in a hospital the point of care at the patient's home by convenient self-administration. In addition, the risk of contaminations and dosing errors is minimized.

Besides these benefits, PFS are associated with complex, process-specific challenges and require adequate product development. A key factor in the development of PFS-based products for parenteral use is the analysis of CCI over its intended shelf-life. A breach of CCI is a significant concern for patient safety.

PFS can be provided in a broad variety of types, most of which have in common that they comprise a syringe 3 having a barrel 30 with a shoulder 303 and a neck 301 extending from the shoulder 303 in the distal direction, a plunger 32 and a syringe closure system, SCS, 4 for closing the front end, that means the distal end, of the syringe 3. The distal end of the syringe 3 can be formed by a needle cannula, NC, 31 or a Luer cone 304. The SCS 4 is a closure system which closes the distal end of the syringe from the outside, that means from in the proximal direction. Thereby, the SCS 4 prevents the fluid contained in the syringe 3, in particular in the barrel 30, from leaking out of the syringe 3 via the distal end. The SCS 4 can be a needle shield, NS, 40 or a tip cap, TIC, 41.

According to a first embodiment, the SCS 4 is a needle shield, NS, 40. The embodiment, where the SCS 4 is a NS 40, is used for PFS, which have a needle cannula, NC, 31 extending distally over the neck 301 of the barrel 30. The NS 40 commonly comprises a rigid cover, RC, 400. The NS 40 sits at least partly on the neck 301 of the barrel 30. There can be means for sealing 402 between the neck 301 of the barrel 30 and the inner circular surface of the proximal end of the NS 40 providing for a sealing of the interior of the syringe 3 against the exterior. The distal portion of the RC 400 is commonly filled with a filling 401, preferably made from an elastic material, such as rubber or silicone. The NC 31 with its open distal end first is inserted into the filling 401, when the NS 40 is slid onto the syringe 3. This insertion of the NC 31 into the filling 401 can provide for a sealing of the interior of the syringe 3 against the exterior. One embodiment of a syringe 3 with a SCS 4, which is a NS 40 is schematically illustrated in FIG. 4a. The axis of the NC 31 is parallel to the axis of the barrel 30 of the syringe 3. The axis of the NC 31 can be offset to the axis of the barrel 30. Preferably, the axis of the NC 31 is identical with the axis of the barrel 30.

In FIG. 4b a second embodiment of a PFS 3 with a SCS 4 which is a tip cap, TIC, 41 is shown. Also in this embodiment the syringe 3 has a barrel 30 with a shoulder 303 and a neck 301 extending from the shoulder 303 in the distal direction, a plunger 32 and a SCS 4 for closing the front end, that means the distal end, of the syringe 3. The neck 301 in this embodiment is a Luer cone 304. In this embodiment usually no needle cannula is provided at the syringe 3 but the distal end of the Luer cone 304 is open. The axis of the Luer cone 304 is parallel to the axis of the barrel 30 of the syringe 3. The axis of the Luer cone 304 can be offset to the axis of the barrel 30. Preferably, the axis of the Luer cone 304 is identical with the axis of the barrel 30. The TIC 41 has a proximal section 412 and an expanded end section 410 which is closed at its distal end. The proximal section of the TIC 41 has a smaller outer diameter than the expanded end section 410. Thereby, a step 411 is formed at the TIC 41.

Some approaches for providing a sealing at a syringe or for leakage testing are known from the prior art. For example, US 2013/041241 A1 discloses a method in which a vapor deposited coating or layer is directly or indirectly applied to at least a portion of the internal wall of the barrel of a capped pre-assembly comprising a barrel and a cap.

EP 2 826 508 A1 discloses a tip cap which comprises: a closed distal end portion having a transverse proximal surface; a peripheral skirt extending in the proximal direction from said proximal surface and having an inner surface designed to cooperate with the outer surface of the injection device tip; a nipple protruding from said proximal surface and designed to engage the injection device tip. A leak test can be conducted according to an extrapolation of ISO 594 standards. In this test, different tip caps are being used and it is checked whether a leakage occurs or not after a predetermined period of time. For one given tip cap, the test is conducted with various insertion depths of the tip cap onto the injection device tip.

WO 2008/012611 A2 discloses a leak testing method for disposable sterile syringes prefilled with a medicinal product, each of which comprises a barrel for containing the medicinal product and a plunger which slides inside the barrel and forms a seal with the latter's inside surface. The method comprises the steps of fixing the position of the plunger relative to the barrel of each syringe to be tested; exposing the syringes to an outside pressure that is different from atmospheric pressure; exposing the syringes to an outside pressure equal to atmospheric pressure; releasing the position of the plunger relative to the barrel of the syringe; and detecting any change in the position of the plunger relative to the barrel of the syringes.

DE 30 44 550 A1 discloses an apparatus for leakage testing of disposable syringes. The apparatus comprises a holding device for holding the cylinder of the syringe by means of a sealing unit for sealing closing the syringe opening, by means of a movement device for moving the piston of the syringe in the cylinder in the direction of the syringe opening and by a detection device for detecting the piston position in the cylinder.

WO 2014/045336 A1 discloses a syringe packaging container with a container body for containing a syringe which has a syringe needle protection cap fitted to the front end of the outer tube of the syringe; a syringe holding section for holding, within the container body, the syringe at a predetermined holding position; and a cap removing section for removing the syringe needle protection cap from the outer tube by separating the outer tube and the syringe needle protection cap from each other, the separation of the outer tube and the syringe needle protection cap being performed by moving the syringe held at the predetermined holding position.

Finally, WO 2012/103140 A1 discloses an apparatus for removal of needle shields from syringes and automatic injection devices. In particular, this document discloses exemplary embodiments which provide a needle shield remover that reliably engages with a distal cap of an automatic injection device and with one or more needle shields coupled to a syringe of the device. When a user removes the distal cap, the needle shield remover reliably removes the needle shields from the syringe, thereby exposing the injection needle for performing an injection. When the apparatus is pulled away from the syringe, the one or more shield engagement mechanisms exert force against the needle shield to remove the needle shield from the syringe. The apparatus may comprise a syringe sleeve housing a syringe that is fitted with a needle shield remover at its distal end. The needle shield remover and the syringe sleeve overlap each other at some portions.

PFS require complex components and manufacturing processes. Compared to a rubber stopper of a conventional vial, small dimensional diversions of the TIC or of the RC of the NS or of the filling of the NS as well as moulding defects may compromise the CCI. PFS featuring a removable SCS, such as a NS or TIC are susceptible to external stress factors with a potential impact on CCI. For example, pressure differences during air shipment can impact the NS position or TIC position and thus CCI.

A few methods are available for container closure integrity tests, CCIT, of PFS, e.g. the microbial container closure integrity test, mCCIT, or physical container closure integrity tests, pCCIT, such as mass spectrometry-based helium leak testing (B. D. Morrical at al, PDA Journal of Pharmaceutical Science and Technology 2007, 61 (4), 226-236). Although there is no clear practical guidance or preference by regulatory authorities for a specific CCIT, the helium leak method is currently the most sensitive CCIT and can be considered as the preferred standard for container closure system, CCS, qualification.

A possible reason for a PFS with SCS to start leaking, may be an external influence, which may exert its effect for example during packaging or transport, and by which the SCS is moved over such a distance that the PFS starts leaking. Therefore, it is desirable to have an indication of the tolerance of the SCS against movement until a leakage of the PFS occurs.

There was a need for a device and a method to allow a reliable detection of leakage of the connection between a SCS and a syringe.

Surprisingly, the problem was solved by providing a device and method for leakage testing wherein the syringe is reliably held and the SCS is moved in a controlled fashion.

ABBREVIATIONS

CCI container closure integrity
CCIT container closure integrity tests
mCCIT microbial container closure integrity tests
pCCIT physical container closure integrity tests
CCS container closure system
COP Cyclo Olefin Polymer
DC displacement cylinder
DD displacement device
DP distance piece
DU displacement unit
HU holding unit
IP insertion pipe
NC needle cannula
NS needle shield
OD opening direction
PAP proximal annular protrusion
PAE proximal annular extension
PFS pre-filled syringe
RC rigid cover
SCS syringe closure system
ST step
ST2 second step
TC test chamber
TIC tip cap
TD testing device
TP transmission piece

SUMMARY OF THE INVENTION

Subject of the invention is a displacement device for providing a displacement of a syringe closure system, SCS, which closes the distal end of the syringe from outside of the syringe, to the syringe in an opening direction, comprising: a holding unit for holding at least part of the syringe and a displacement unit, which is movably attached to the holding unit for movement by a predetermined distance in the opening direction, wherein the holding unit comprises a receiving cylinder for receiving at least part of the barrel of the syringe and a clamping element for clamping at least part of the flange of the syringe between the clamping element and the receiving cylinder and wherein the displacement unit comprises a displacement cylinder movably attached to the receiving cylinder by a screw type connection.

DETAILED DESCRIPTION OF THE INVENTION

With the DD according to the invention a SCS which is provided on the distal end of a syringe can be displaced in an opening direction. The opening direction is parallel to the axis of the barrel and is the direction in which the SCS is moved away from the barrel of the syringe. The holding unit, HU, of the DD serves for holding at least part of the syringe. The displacement unit, DU, is movably attached to the HU. The movable attachment of the DU allows for a movement by a predetermined distance in the opening direction. When the syringe with the SCS is provided in the DD, the SCS is in contact with the DU and by moving the DU also the SCS is moved by the predetermined distance in the opening direction. The HU comprises a receiving cylinder, which serves for receiving at least part of the barrel of the syringe. In particular, the part of the barrel which is adjacent to the flange of the syringe is received in the receiving cylinder. The holding unit further comprises a clamping element. The clamping element serves for clamping at least part of the flange of the syringe between the clamping element and the receiving cylinder.

The DU comprises a displacement cylinder, DC, movably attached to the receiving cylinder. The DC is attached to the receiving cylinder in such a way, that it can be moved in the axial direction of the receiving cylinder, in particular in the opening direction In particular, the DC is movably attached to the receiving cylinder by a screw type connection.

By clamping at least part of the flange, preferably at least the outer diameter of the flange between the clamping element and the receiving cylinder, the barrel of the syringe is securely held in the DD. In particular, the barrel is prevented from axial movement in the DD and in particular in the receiving cylinder. Furthermore, by this clamping, the axis of the barrel of the syringe and thereby the opening direction is parallel to or is in the direction of the movement of the DU, which is a decisive prerequisite for the functioning of the DD. In addition, also a rotation of the barrel in the receiving cylinder is prevented by clamping the flange. This secure holding of the barrel of the syringe in the DD is advantageous, as the movement of the SCS in the opening direction does not lead to a movement of the barrel, and the distance by which the SCS is moved relative to the barrel of the syringe can therefore be determined precisely.

The clamping element may have different shapes. Preferably, the clamping element has a ring shape, that means it has a through hole along the axis of the clamping element. Preferably, the clamping element has a cylindrical body. The clamping element and the receiving cylinder may be connected in different ways as long as these components of the HU apply a clamping force on the flange of the syringe. For example, the clamping element may be attached to the receiving cylinder by a biasing clip.

Preferably, the through hole of the clamping element has a diameter which is larger than or equal to the inner diameter of the barrel of the syringe but is smaller than the outer diameter of the flange of the syringe to be held in the DD.

Preferably, the receiving cylinder and the clamping element are connected by a screw type connection. This type of connection is advantageous, since the clamping force, which is applied on the flange of the syringe held between the receiving cylinder and the clamping element, can be accurately adjusted. Thereby, syringes having flanges of different thicknesses can be securely held in the DD without damaging the flange. In addition, the clamping force may be strong enough to hold the syringe in the DD without the need to further support the barrel of the syringe in the DD, for example in the receiving cylinder. Thereby the barrel can have the same or a smaller outer diameter than the inner diameter of the receiving cylinder.

Preferably, the outer diameter of the clamping element in a distal section thereof corresponds to the inner diameter of the receiving cylinder in a proximal section thereof. Thereby, the distal part of the clamping element can be received in the proximal part of the receiving cylinder.

If not defined differently, the term distal denotes the direction from the flange of the syringe towards the neck of the syringe held in the DD and the term proximal denotes the opposite direction. If not defined differently, the axial direction denotes the direction of the axis of the barrel of the syringe held in the DD, which is also the opening direction. Preferably, the axis of the clamping element and the axis of the receiving cylinder have the same direction, which is also the opening direction.

Preferably, the distal end of the clamping element acts as a clamping surface and a proximal inner surface of the receiving cylinder acts as counter surface. Thereby, the flange can be held between the clamping surface and the counter surface. As the surfaces are at the distal end of the clamping element and at a proximal inner surface of the receiving cylinder, respectively, the clamping force acts at least partially in the axial direction of the syringe and thereby prevents axial movement of the syringe in the opening direction.

According to one embodiment, the proximal inner surface is perpendicular to the axis of the receiving cylinder.

According to a preferred embodiment, the proximal inner surface is tilted to the axis of the receiving cylinder.

In both cases, that means with the proximal inner surface being perpendicular or being tilted to the axis of the receiving cylinder, the clamping surface is preferably perpendicular to the axis of the clamping element and thereby perpendicular to the axis of the receiving cylinder. In the first case, the clamping surface and the proximal inner surface are parallel to each other. The flange received between these surfaces will therefore be in contact with both surfaces over its opposite surfaces which are perpendicular to the axis of the receiving cylinder. In the second case, where the proximal inner surface is tilted to the axis of the receiving cylinder, the proximal surface of the flange which is perpendicular to the axis of the clamping element will be in contact with the clamping surface, while only the circumference of the distal surface of the flange will be in contact with the proximal inner surface. In this second case, the barrel of the syringe will be aligned with the axis of the clamping element and thereby with the axis of the receiving cylinder only by clamping the flange. The barrel in that case does not need to be supported by the inner diameter of the receiving cylinder. Thereby the barrel can have the same or a smaller outer diameter then the smallest inner diameter of the receiving cylinder. The second case is a preferred embodiment.

Preferably, the smallest inner diameter of the receiving cylinder is larger than or equal to the outer diameter of the barrel of the syringe but smaller than the outer diameter of the flange of the syringe to be held in the DD.

According to one embodiment, the receiving cylinder has an expanded section at the proximal end with the inner diameter being larger than the inner diameter of the distal section of the receiving cylinder and the outer diameter of the expanded section being larger than the outer diameter of the distal section of the receiving cylinder. This design of the receiving cylinder allows for the proximal section to receive within the inner diameter the clamping element while the distal section may receive a DC as part of the DD, on its outside. The axis of the DC is parallel to the axis of the DD, in particular these two axes are aligned when the receiving cylinder has received the DC on its outside.

According to one embodiment, the clamping element has a cylindrical body with a thread extending over part of the length of the clamping element for screw type connection to the receiving cylinder. The thread is preferably an outer thread.

According to one embodiment, the clamping element has at least one recess on the outer circumference. The outer circumference may be a ring, for example a toothed ring. By providing at least one recess on the outer circumference, the clamping element can be easily handled. In particular, screwing-in of the clamping element into the receiving cylinder is facilitated.

According to one embodiment, the receiving cylinder has an inner thread at a proximal section thereof. The inner thread at the proximal section may be used for screw type connection with the clamping element.

According to one embodiment, the receiving cylinder has an outer thread at a distal section thereof. The outer thread may be used for screw type connection with a part of the DU.

According to one embodiment, the DC has an inner thread for screw type connection to the receiving cylinder. By providing a screw type connection between the DC and the receiving cylinder, the DC can be axially moved by rotating the DC on the receiving cylinder. The pitch of the thread will define the axial movement. Such an axial movement can be performed in small steps, that means that the DC can be moved axially in small distances in the opening direction. This is advantageous, as the distance, by which the DC is moved, defines the distance by which the SCS will be moved in the opening direction.

Preferably, the DU comprises a transmission piece, TP, for transmitting axial movement from the DC to the SCS in the opening direction. The TP is preferably not firmly attached to the DC. In particular, the TP does not perform rotational movement, when the DC is rotated.

Preferably, the TP is a body with in inner opening. The TP preferably has a circular shape. The inner opening is preferably provided at the centre of the TP. The inner opening, however, may also be provided offset to the centre of the TP, that means may be positioned eccentrically.

According to one embodiment, the inner opening has the shape of a cylindrical hole. Preferably, the TP has the shape of a ring body with an outer diameter lager than the diameter of the inner opening. Preferably, the TP has a proximal annular protrusion, PAP, along the outer circumference of the ring body. The PAP extends in the proximal direction and has an inner diameter which is larger than the inner diameter of the inner opening but smaller than the outer diameter of the TP. Thereby, a step, ST, between the inner opening of the TP and the inner diameter of the PAP is formed. The TP in this embodiment has the shape of a cap.

Preferably, the outer diameter of the TP is larger than the outer diameter of the DC. Preferably, the DC ends at its distal end with a planar area with the shape of a ring which is perpendicular to the axis of the DC. The inner diameter of the PAP, preferably, corresponds to the outer diameter of the DC, in particular the inner diameter of the PAP is equal to the outer diameter of the DC or is slightly larger than the outer diameter of the DC. Thereby, the TP can be placed on the distal end of the DC and the ST will be in contact with said planar area at the distal end of the DC. In addition, the inner diameter of the PAP will be in contact with the outer diameter of the DC. Thereby tilting of the TP on the DC can be avoided and the TP sits preferably on the DC with a snug fit without clearance.

In the embodiment, where the inner opening of the TP has the shape of a cylindrical hole, the inner diameter of the inner opening is equal to or larger than the outer diameter of the barrel of the syringe which is to be held in the DD. Preferably, the inner diameter of the inner opening is larger than the outer diameter of the barrel of the syringe.

Preferably, where the inner opening of the TP has the shape of a cylindrical hole, the inner diameter of the inner opening is smaller than the largest diameter of the SCS. Where the SCS is a NS, the largest diameter of the SCS is the proximal diameter of the NS. Where the SCS is a TIC, the largest diameter of the SCS is the diameter of the expanded end section of the TIC. This embodiment can preferably be used for a syringe with a SCS having a largest diameter which is larger than the outer diameter of the barrel of the syringe.

In one embodiment, a collar is provided at the distal end of the inner opening of the TP extending radially inwards from the inner diameter of the inner opening. The outer diameter of the collar thus corresponds to the inner diameter of the inner opening. The inner diameter of the collar is smaller than the inner diameter of the inner opening. Thereby, the collar creates a second step ST2, having a circular shape. This embodiment can preferably be used for a syringe with a SCS having a largest diameter which is smaller than the outer diameter of the barrel of the syringe.

According to one embodiment, the inner diameter of the collar corresponds to the neck of the barrel of the syringe. The inner diameter of the collar is equal to or larger than the neck of the barrel of the syringe. The inner diameter of the collar is smaller than the shoulder of the barrel of the syringe. Thereby, the neck of the syringe can pass through the collar of the TP and the second step ST2 can rest on the distal end of the barrel, in particular the shoulder of the barrel, which is proximal to the neck.

According to one embodiment, the inner diameter of the collar is smaller than the largest diameter of the SCS.

Preferably, the TP has a slot at the distal end with a direction perpendicular to the axis of TP. The slot extends from the inner diameter of the inner opening and where provided from the inner diameter of the collar to the outer diameter of the TP over the entire radius of the TP and it is open at its peripheral end. The slot extends axially over the entire ring body, that is it also extends over the collar and the PAP.

Preferably, the slot has a width which corresponds to, in particular is equal to, the inner diameter of the inner opening of the TP. Where a collar is provided on the distal end of the inner diameter of the inner opening, the slot has a width which corresponds to the inner diameter of the collar. Thereby, the TP can be slid onto the DC already containing the syringe from the side and can be brought in contact with the SCS.

According to one embodiment, the width of the slot and the inner diameter of the inner opening or the inner diameter of the collar correspond to or are larger than the neck of the barrel of the syringe.

According to a further embodiment, the width of the slot and the inner diameter of the inner opening or the inner diameter of the collar correspond to or are larger than the outer diameter of the proximal section of a TIC on the neck of the syringe and smaller than a distal expanded section of the TIC.

According to one embodiment, the section of the slot which extends in axial direction through the ring body and the PAP of the TP has width which is larger than the width of the section of the slot extending along the distal end of the TP. In particular, the width of the slot at the distal end of the TP corresponds to the inner diameter of the collar and the width of the slot extending in the axial direction corresponds to, that means is equal to or larger than, the inner diameter of the inner opening. Thereby, the TP can be slid on to a syringe already received in the receiving cylinder from the side.

According to the embodiment, where the SCS is a NS, the neck of the barrel of the syringe will be received in the inner diameter of the TP. Subsequently, the DC can be moved in an axial direction towards the TP, which is the opening direction, so that the PAP surrounds the distal end of the DC. When the DC is moved further in the opening direction, the ST of the TP will come to sit on the DC. When the DC is moved even further, the TP sitting on the DC is also moved in the opening direction and eventually the distal end of the TP will touch the proximal end of the NS. When the DC is moved even further, the movement will begin to move the NS sitting on the TP, which again sits on the DC.

According to an embodiment, where the SCS is a TIC, the outer circumference of the proximal section of the TIC is received in the inner diameter of the TP. Subsequently, the DC can be moved in an axial direction towards the TP, which is the opening direction, so that the PAP surrounds the distal end of the DC. When the DC is moved further in the opening direction, the ST of the TP will come to sit on the DC. When the DC is moved even further, the TP sitting on the DC is also moved in the opening direction and will slide along the proximal section of the TIC. Eventually, the distal end of the TP will touch the step of the TIC and become in contact with the proximal end of the expanded end section of the TIC. When the DC is moved even further, the movement will begin to move the TIC sitting on the TP, which again sits on the DC.

The movement of the TIC or NS will be relative to the barrel of the syringe in the opening direction, as the barrel of the syringe is fixed via the flange of the syringe, which is held between the clamping surface of the clamping element and the counter surface of the receiving cylinder, and thereby the TIC or NS will be displaced from the syringe in the opening direction and no longer sit in its initial position on the syringe.

According to one embodiment, at least the distal end of the DC has a friction reducing coating. By providing a coating which reduces friction onto at least the distal end of the DC, transmission of rotational movement of the DC to the TP, which is in contact with the DC, can be avoided.

According to one embodiment, in addition or alternatively to the distal end of the DC, at least the proximal surface of the TP has a friction reducing coating. Thereby, transmission of rotational movement of the DC to the TP can be further avoided.

According to one embodiment, the TP has a circumferential ball bearing, this circumferential ball bearing being in a plane perpendicular to the axis of the TP. The ball bearing can be an axial deep groove bearing. In the embodiment, where the TP has a circumferential ball bearing, the TP is axially made out of two parts, each with the shape of a ring, and which can be rotated against each other due to the connecting ball bearing. One part is the distal part towards the SCS, the other is the proximal part towards the DC. The proximal part sits on the DC, the distal part comes into contact with the SCS. Thereby, when the DC is rotated there will be no rotation of the part of the TP towards or in contact with the SCS, thereby the SCS will not be rotated when the TP is moved in the opening direction by the rotation of the DC. This embodiment of the TP has advantages when the SCS or at least the proximal part of the SCS is made out of a material with a high friction, such as rubber.

Preferably, at least one scale marking is provided on at least part of the outer circumference of the DC and on the outer circumference of the receiving cylinder. By providing a scale marking on both the DC and the receiving cylinder, the rotational angular movement of these two cylinders relative to each other can be determined. As the DC and the receiving cylinder are preferably attached to each other by means of screw type connection with a thread with a respective lift per angular movement, the relative rotational movement corresponds to an axial movement and thereby the distance, by which the DC has moved in the opening direction, can be derived from the relative position of the scale markings on the cylinders.

According to one embodiment, the scale marking is a reference marking or a number of scale markings are provided to form a scale.

According to one embodiment, the largest outer diameter of the receiving cylinder corresponds to the outer diameter of the DC; more preferably, these two diameters have the same size. Preferably, the scale on the DC and the scale on the receiving cylinder match with each other. Preferably, the markings of the scales which are provided on the outside of each of the two cylinders will be in close vicinity to each other and the relative rotational movement of the cylinders can easily be determined.

Preferably any parts of the DD are made of metal or rigid plastic, more preferably of metal, such as aluminium or steel such as stainless steel. Preferably, the DD or its parts are made of aluminium.

A further subject of the invention is a testing device, TD, for leakage testing of a connection of a SCS for a syringe with the syringe, wherein the testing device comprises a displacement device according to the invention.

Preferably, the TD comprises an insertion pipe, IP, for insertion into the barrel of the syringe, in particular into the lumen of the barrel. The IP is preferably made of metal, such as aluminium or steel, more preferably of stainless steel.

Preferably, the IP has a channel extending through the IP for providing fluid connection between the lumen of the barrel and a detection unit.

According to one embodiment, the TD comprises a body having a channel extending through the body and connecting the channel of the IP with the detection unit. Vacuum may be generated by the TD and applied in the channel of the body and the channel of the IP and thereby to the lumen of the syringe.

According to one embodiment, the IP is attached to the body of the TD. In particular, the IP is attached to a side of the body.

Preferably, the TD comprises a distance piece, DP, movably attached to the IP for setting and holding a distance between the distal end of the IP and the distal end of the lumen of the barrel of the syringe. By setting and holding a distance between the distal end of the IP and the distal end of the lumen, damaging of the barrel by the IP can be avoided. Such damaging may occur, once vacuum is applied in the channel of the IP. Without the DP, the barrel of the syringe would be drawn along the IP by the vacuum and the distal end of the IP would penetrate through the distal end of the barrel.

According to one embodiment, the IP has an outer thread and the DP is a nut fitting to the outer thread of the IP. In one embodiment the outer diameter of the nut corresponds to the proximal outer diameter of the clamping element. Thereby, clamping element and thus the DU can sit on the nut. This allows for the DP to be moved in the axial direction of the IP, in particular in the distal direction, in a controlled fashion and thus allows for the distance between the distal end of the IP and the distal end of barrel of the syringe to be adjusted and held.

According to one embodiment, the clamping element has a proximal annular extension, PAE, with an inner diameter larger than the inner diameter of the through hole of the clamping element. Preferably, the axial length of the PAE of the clamping element is equal to or smaller than the axial dimension of the DP. Preferably, the outer diameter of the DP, preferably in form of said nut, is equal to or smaller than, preferably equal to, the inner diameter of the PAE of the clamping element. Thereby the clamping element can slide onto the DP. This provides for a reduction of any tilting movement or any movement perpendicular to the axis of the receiving cylinder of the DD holding the syringe when the barrel of the syringe has been slid onto the IP. In case of equal diameters any such movement is avoided. This contributes to the efficiency and reliability of the sealing of interior of the barrel of the syringe, which can be provided by a sealing of the IP, in particular by a sealing head of the IP.

According to one embodiment, the IP has at least one sealing ring arranged at the outer circumference of the distal end of the IP. According to one embodiment, the IP has a sealing head at its distal end and at least one sealing ring, is attached to the sealing head. The at least one sealing ring is attached to the outer circumference of the sealing head. Thereby, once the IP with the sealing head is inserted into the lumen of the barrel, the section of the lumen of the barrel distal to the sealing head is separated from the section proximal to the sealing head. In addition, the sealing head with its sealing ring(s) provides for securely holding the syringe on the TD. The syringe is held on the TD via the sealing ring which is in contact with the inner diameter of the barrel of the lumen and via the flange of the syringe which is held between the clamping element and the receiving cylinder of the DD which in turn are held in an axial position on the IP by the DP.

One, two, three or four, sealing rings are attached to the sealing head. Preferably, two or three sealing rings are attached to the sealing head.

In one embodiment, the sealing head is a part separate from the IP and can be screw onto the IP. Preferably the sealing head is screwed onto the distal end of the IP and has a channel going through it, which is in fluid connection with the channel of the IP and thereby provides for an extension of the channel of the IP into the lumen of the barrel of the syringe. That means, that the channel of the sealing head provides for a fluid connection of the lumen of the barrel with the channel of the IP.

When the sealing head is a part separate from the IP, the size, in particular the diameter, more in particular the outer diameter of the sealing ring, of the sealing head can be adjusted according to the inner diameter of the barrel of any syringe. Thereby, the same TD can be used for syringes of various diameters, except for the sealing head which is then the only part that needs adaption to the size of the barrels of the syringes.

Preferably, the outer diameter of the at least one sealing ring corresponds to the inner diameter of the barrel of the syringe, preferably it is larger than the inner diameter of the barrel of the syringe and the sealing ring is made of an elastic material. Thereby, the syringe can be securely held on the IP. In addition, the lumen of the barrel of the syringe is thereby divided into two parts, a part on the proximal side of the sealing ring which is in fluid connection with the exterior of the syringe, and a part on the distal side of the sealing ring, which is sealed from the exterior.

According to one embodiment, two or three sealing rings are attached to the sealing head with a axial distance to each other, the axial distance contributes to the securely holding of the syringe on the IP without any tilting movement or any movement perpendicular to the axis of the receiving cylinder of the DD holding the syringe, when the barrel of the syringe has been slid onto the IP.

Preferably, the TD comprises a test chamber, TC, detachably connected to the body of the TD. The TC is sized such that at least the IP and the DD can be inserted into the TC.

Preferably, the configuration of the connection between the TC and the body of the TD provides for sealing of the inside of the TC from the exterior, once the TC is connected to the body of the TD.

Preferably, the TC comprises an inlet for input of a testing medium. By inputting testing medium into the TC, the syringe with the SCS which is disposed in the DD and placed onto the IP in the TC will be surrounded by the testing medium, which means that the exterior of the syringe in the TC will be at least partially filled with testing medium.

The testing medium may be but is not limited to a test gas, preferably the test gas is a rare gas such as helium, argon or hydrogen, more preferably the test gas is helium.

The detection unit is configured to detect testing medium.

Preferably, the detection unit comprises a mass spectrometer.

Preferably the TC comprises also an outlet for outlet of the testing medium. Thereby, the conditions, in particular pressure conditions in the TC can be adjusted.

According to one embodiment, the body of the TD has a protrusion for attaching the TC.

According to one embodiment, the IP is attached to the protrusion. Thereby, the TC can reliably be placed around a DD which is positioned on the IP.

A further subject of the invention is a method for leakage testing of a connection of a SCS for a syringe with the syringe, wherein the method is carried out with a testing device according to the invention with a displacement device according to the invention.

Preferably, the method comprises the steps of:
a) placing a syringe with a SCS in a DD according to the invention,
b) placing the DD on a TD according to the invention,
c) placing a TC over the DD,
d) evacuating a part of the lumen of the syringe,
e) exposing the syringe to testing medium, and
f) measuring the amount of testing medium at a detection unit of the TD, which has passed through any leakage between the SCS and the syringe.

Preferably, step a) comprises the steps of:
a1) inserting the receiving cylinder into the DC,
a2) inserting the syringe with the SCS from the proximal end of the receiving cylinder into the receiving cylinder,
a3) clamping the flange of the syringe barrel to the receiving cylinder, and
a4) attaching the TP to the distal end of the DC.

According to one embodiment, step a) comprises a step a5) of
positioning the TP into an initial position, wherein the TP abuts to the proximal end of the largest diameter of the SCS without applying force to the SCS, by moving the DC relative to the receiving cylinder in the OD.

According to one embodiment, step a3) comprises the step of
screwing a clamping element into the proximal end of the receiving cylinder until the clamping surface of the clamping element abuts with the proximal side of the flange of the syringe and clamps the flange between the clamping surface and counter surface.

Preferably, step b) comprises the step of:
b1) inserting an IP of the TD into the lumen of the syringe barrel.

Preferably, step b) comprises the step of:
b2) advancing the IP in the lumen of the barrel of the syringe into the vicinity of the shoulder of the barrel of the syringe.

According to one embodiment, step b) comprises the step of:

b3) moving the DP on the IP to a position, wherein the proximal side of the DD is in contact with the distal side of the DP.

Preferably, step d) is carried out by applying vacuum to the lumen of the barrel via the IP. Preferably, step d) is carried out after positioning the TP into an initial position, wherein the TP abuts to the proximal end of the largest diameter of the SCS without applying force to the SCS. Once vacuum is applied, the TP and thus the DD will ensure that the SCS is not drawn or sucked towards the barrel of the syringe. This is in particular, important for embodiments where the SCS is a TIC. The TIC covers the Luer cone of the syringe, which has a hole at its distal end. As the hole of the Luer cone is larger than the hole in a NC, vacuum applied to the lumen of the syringe will apply a pulling or sucking force onto the TIC. When vacuum is applied to the lumen of the syringe, with the TP being in the initial position, the DD and in particular the TP will act against such pulling or sucking force TIC and the DD in that stage acts as a holding device.

The evacuation of the lumen of the barrel may be performed by the detection device, or by a further device, such as a conventional vacuum pump. Preferably, the pressure inside the syringe is less than 100 mbar, more preferably less than 50 mbar, even more preferably less than 25 mbar, especially less than 20 mbar, more especially less than 10 mbar, even more especially less than 5 mbar, in particular less than 1 mbar.

According to one embodiment, step e) is performed by exposing the exterior of the syringe in the TC to an atmosphere comprising the testing medium. More preferably, the exterior is exposed to an atmosphere comprising at least 50%, even more preferably, at least 75%, especially at least 80%, more especially at least 85%, even more especially at least 90%, in particular at least 95%, of testing medium, the % being % by volume based on the total volume of the atmosphere to which the exterior of the syringe is exposed to.

The exposure of the exterior of the syringe to an atmosphere of testing medium can be realized by exposing the exterior of the syringe to a constant flow of the testing medium in the TC. Preferably, the TC is flooded by a constant flow of the testing medium at or above atmospheric pressure.

The method and TD according to the invention provide the possibility for reliably correlating the flow rate or leakage rate of testing medium into the lumen of the syringe via any leakage between the SCS and the syringe with the distance by which the SCS has been moved in the opening direction.

The distance is preferably measured in mm and the leakage rate is preferably measured in mbar*l/s.

According to one embodiment, the method further comprises the step of g1) determining whether the measured amount of testing medium which entered the lumen of the barrel exceeds a pre-set threshold value.

In this embodiment, also the distance by which the SCS has been moved in the opening direction from the barrel will be measured and the result of the leakage testing method will be the distance at which the threshold value of testing medium, which has entered the lumen of the barrel, has been reached or exceeded.

According to an alternative embodiment, the method comprises the step of g2) verifying whether the measured amount of testing medium exceeds a pre-set threshold value at a pre-set distance of the SCS from the initial position in the opening direction.

In this embodiment, the SCS will be moved in the opening direction by the pre-set distance and it will then be verified whether the amount of testing medium which entered the lumen of the barrel exceeds a pre-set threshold value or whether the amount is below the pre-set threshold value. For example, a maximal displacement of the SCS in mm up to a leakage or leakage rate of $>6\times 10^{-6}$ mbar l/s may be verified.

The threshold value of the amount of testing medium and/or the pre-set distance of the SCS at which the threshold value is not reached, may be pre-set by a legislative body and be standardized. The present invention can then be used for reliably determining whether a PFS with a SCS complies with the standard. The threshold value and the pre-set distance may comprise tolerances.

Preferably, the method further comprises the steps of:

h) moving the DC in the opening direction by a predetermined distance relative to the receiving cylinder.

Preferably, the method further comprises the steps of i) removing the TC before step h) and j) placing the TC after step h).

Preferably, the method further comprises the step of k) determining the distance between the initial position of the DU and the position of the DU, where the threshold value has been exceeded;

preferably the distance between the initial position of the TP and the position of the TP, where the threshold value has been exceeded.

Preferably, step k) is performed by reading the scale on the DD.

Preferably, the method comprises the step of:

l) removing the plunger from the syringe before placing the syringe on the TD, preferably before step a).

The method is carried out with the plunger of the syringe being removed from the syringe, so anywhere in the description when the syringe is mentioned it refers to a syringe without its plunger.

BRIEF DESCRIPTION OF THE DRAWINGS

The present invention will be described again with reference to the enclosed drawings, wherein:

FIG. 1b: shows a schematic sectional view of the embodiment of the testing device according to FIG. 1a;

FIG. 2b: shows a schematic sectional view of the embodiment of the testing device according to FIG. 2a;

DETAILED DESCRIPTION OF PREFERRED EMBODIMENTS

Figure 1A:
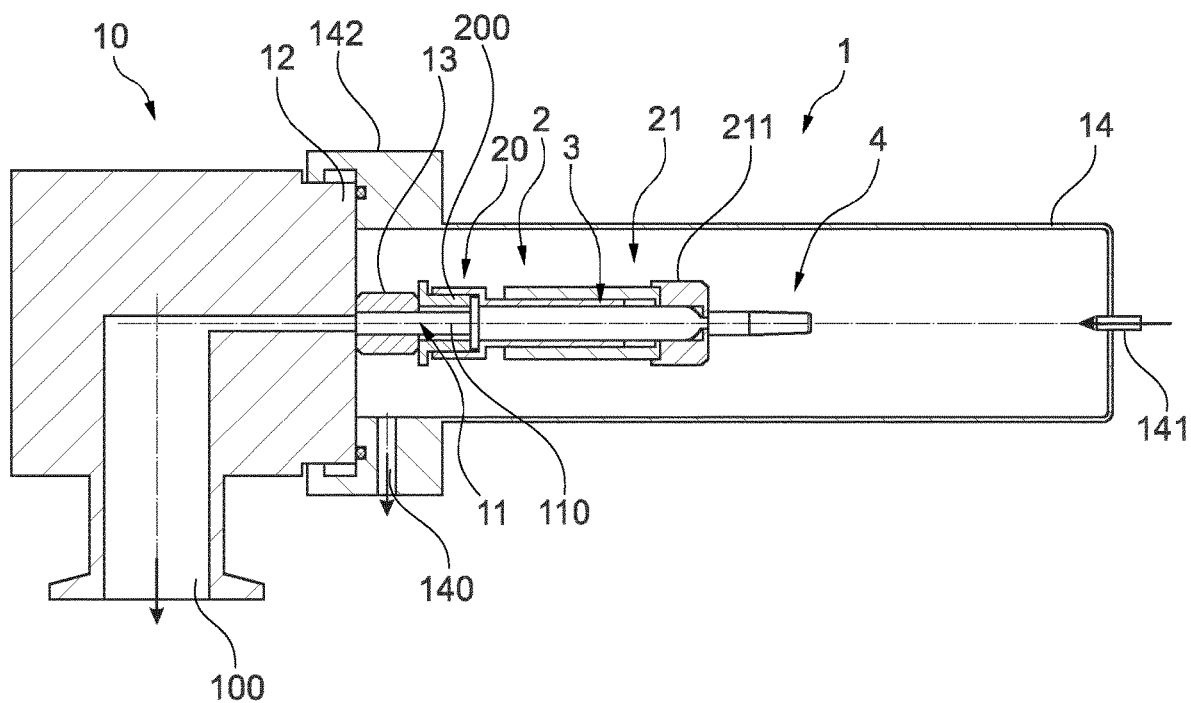
FIG. 1a: shows a schematic, partial sectional view of an embodiment of the testing device according to the invention.

The present invention will now be described in more detail with reference to the enclosed figures. Same components and arrangements are denoted in the figures by the same reference numerals and the respective description may be omitted in order to avoid redundancies.

Features and advantages which are described with respect to the displacement device also apply to the testing device and the method for testing and vice versa and are only described once.

Figure 1B:
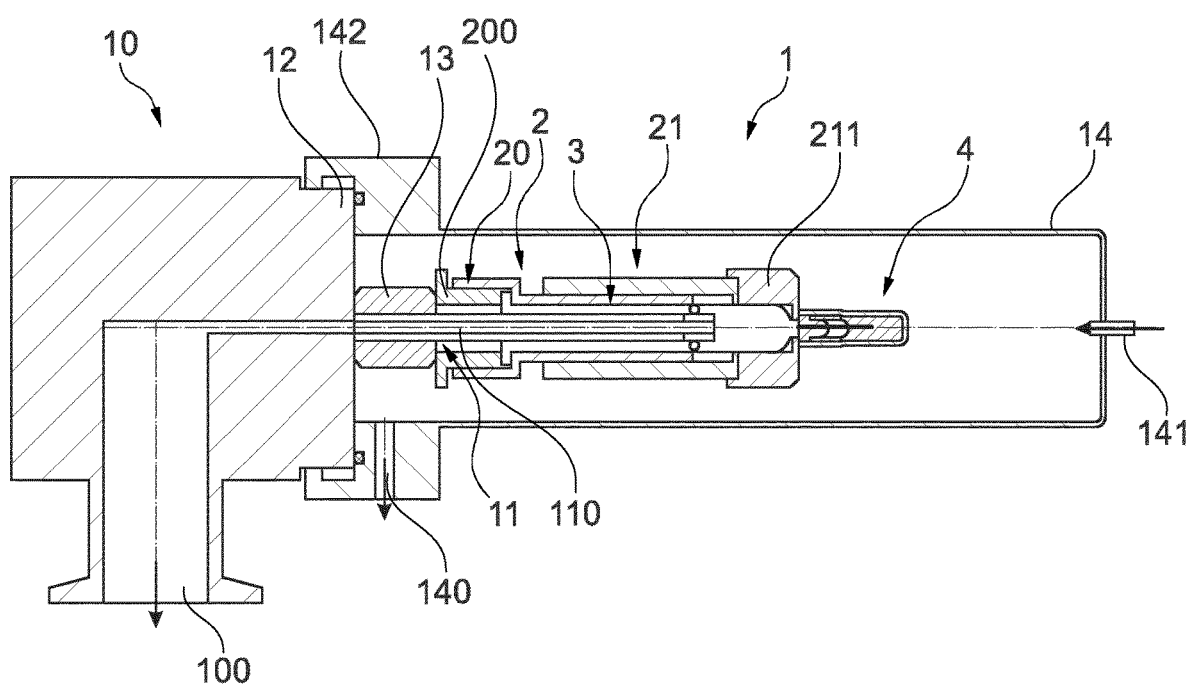

In FIG. 1a and FIG. 1b one embodiment of the TD 1 for leakage testing of a connection of a NS 40 for a syringe 3 with the syringe 3 is shown. The TD 1 comprises a body 10 and a DD 2. The body 10 has a protrusion 12 on one side. Attached to the protrusion 12 is a TC 14. The TC 14 has an attachment element 142 for detachably attaching the TC 14 to the protrusion 12. The attachment element comprises means for sealing the interior of the TC 14 against the exterior of the TC 14 once the TC 14 is attached to the protrusion 12. The TC 14 also has an inlet 141 for testing medium and an outlet 140 for testing medium.

In the body 10 of the TD 1 a channel 100 is formed. The channel 100 provides fluid connection of a detection unit (not shown) with a channel 110 extending through an IP 11 (see FIG. 1b). The detection unit is used for detecting the presence of testing medium that has passed through NC 31 of the syringe 3 due to a leakage between the connection of the NS 40 and the syringe 3.

In FIG. 1b the embodiment of the TD 1 of FIG. 1a is shown with the syringe 3, the IP 11 and the NS 40 in sectional view. The IP 11 is attached to the protrusion 12. On the IP 11, the DD 2 is positioned. The detection unit is in fluid communication with the interior of the barrel 30 of the syringe via channel 100 in the body 10 of the TD 1 and channel 110 of the IP 11. As can be derived from FIG. 1b, the channel 110 of the IP 11 extends through the length of the IP 11. At the distal end of the IP 11 a sealing head 111 is provided. The channel 110 also extends through the sealing head 111. In the depicted embodiment, a sealing ring 112 is provided on the outside of the sealing head 111. The sealing ring 112 is preferably received in a groove (not shown) on the circumference of the sealing head 111. Even though only one sealing ring 112 is shown in FIG. 1b, the sealing head 111 may be provided with more than one, for example two or three sealing rings 112. The sealing head 111 may be screwed onto the distal end of the IP 11.

Between the DD 2 and the protrusion 12 of the body 10 the DP 13 is positioned.

Figure 2A:
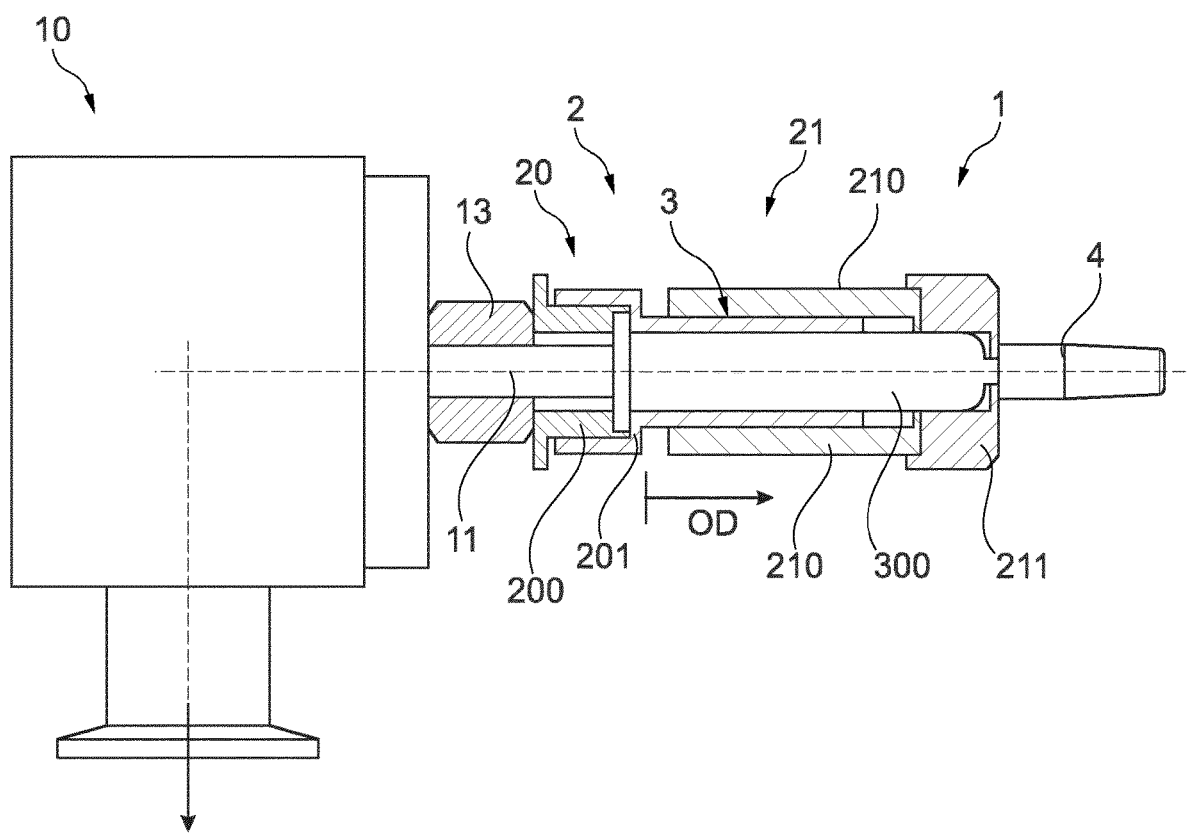
FIG. 2a: shows a schematic, partial sectional view of the embodiment of the testing device according to FIG. 1a without the testing chamber.
Figure 2B:
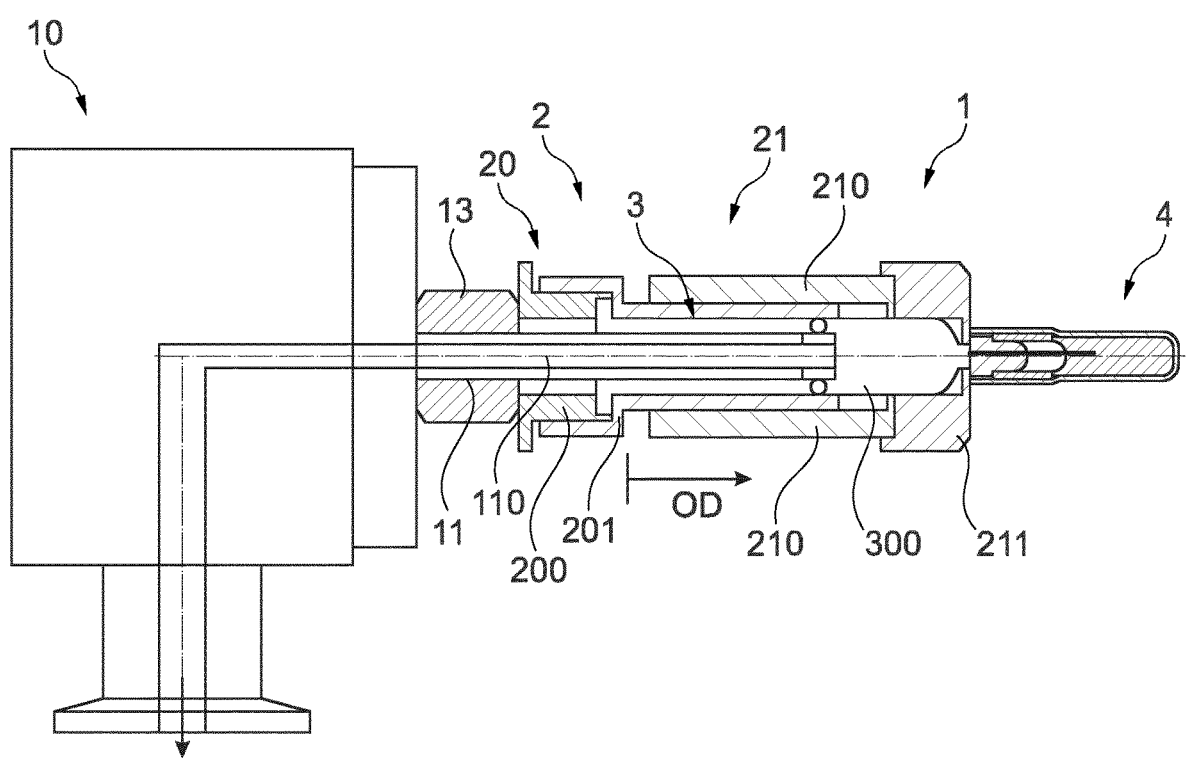

The assembly of the DD 2 can be better seen in FIG. 2a and in FIG. 2b, where the TD 1 is shown without TC 14, and in FIGS. 5 to 10.

Figure 5A:
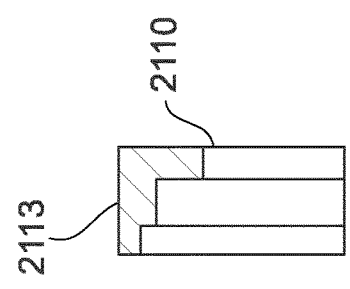
FIG. 5a: shows a sectional view of the components of a first embodiment of the displacement device according to the invention.
Figure 5A:
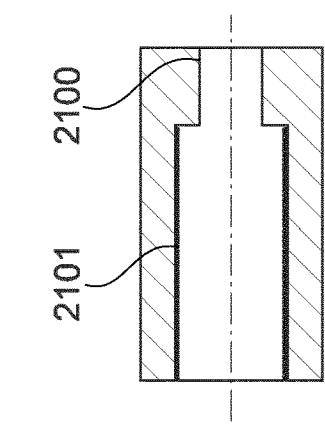
Figure 5A:
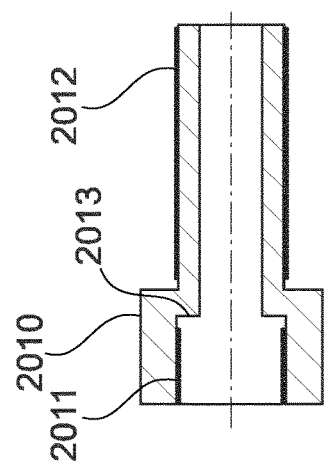
Figure 5A:
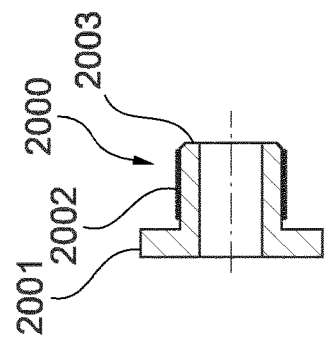
Figure 5B:
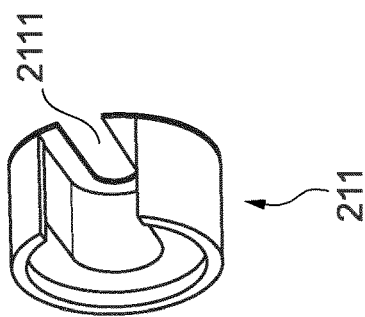
FIG. 5b: shows a perspective view of the components of the first embodiment of the displacement device as a graphical depiction.
Figure 5B:
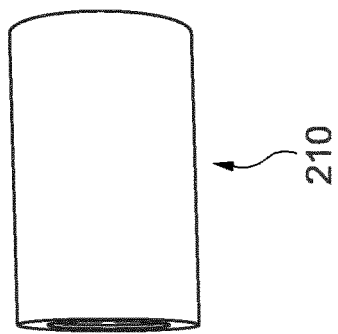
Figure 5B:
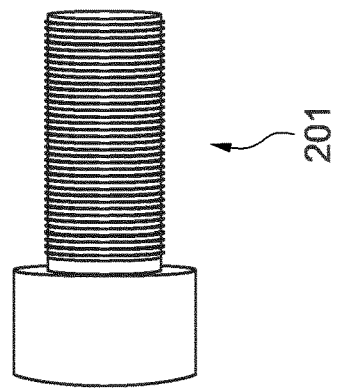
Figure 5B:
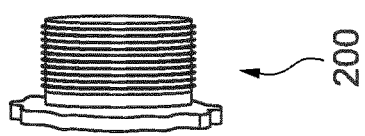
Figure 6:
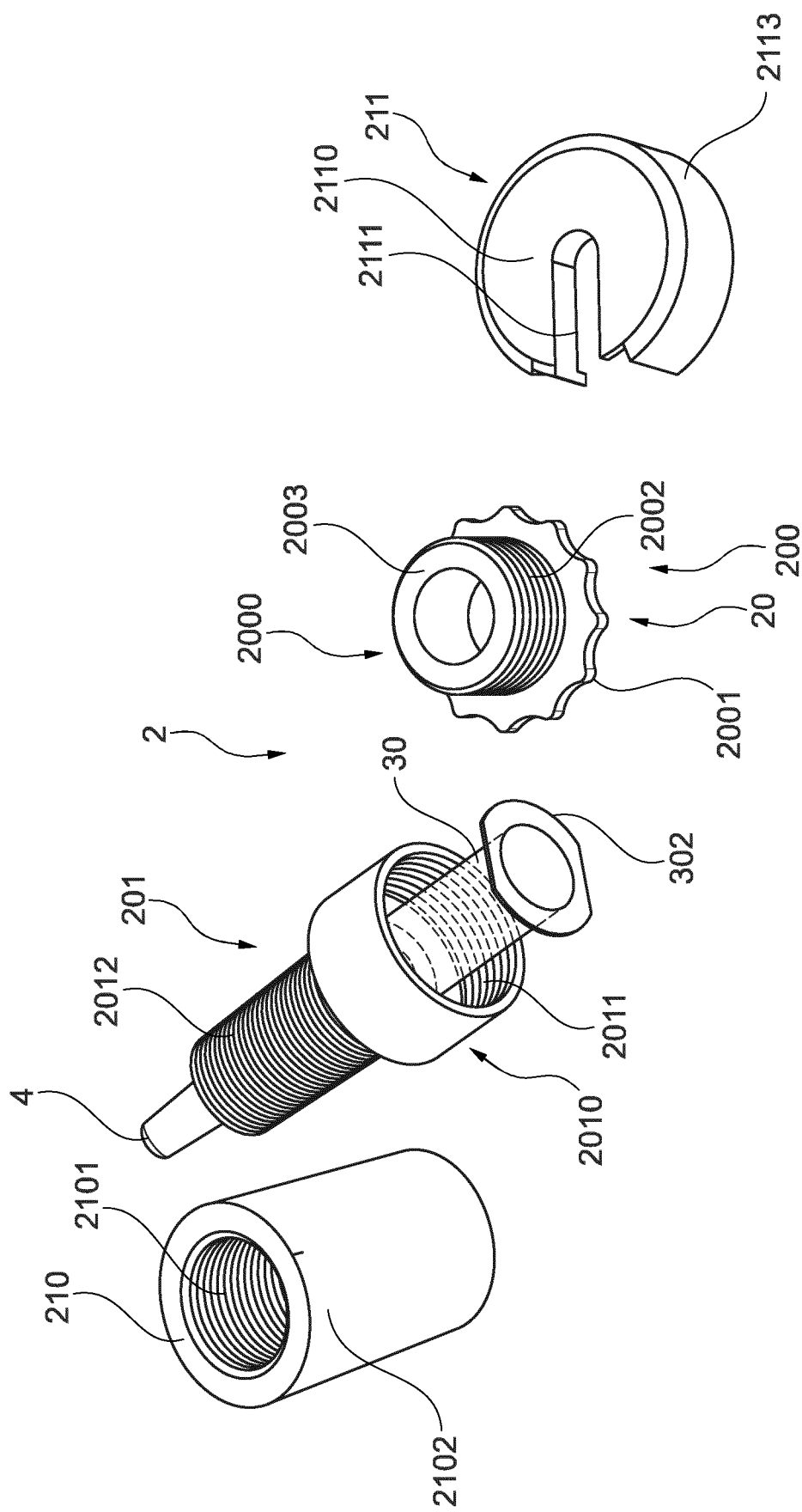
FIG. 6: shows another perspective view of the components of the first embodiment of the displacement device with a syringe as a graphical depiction.
Figure 7:
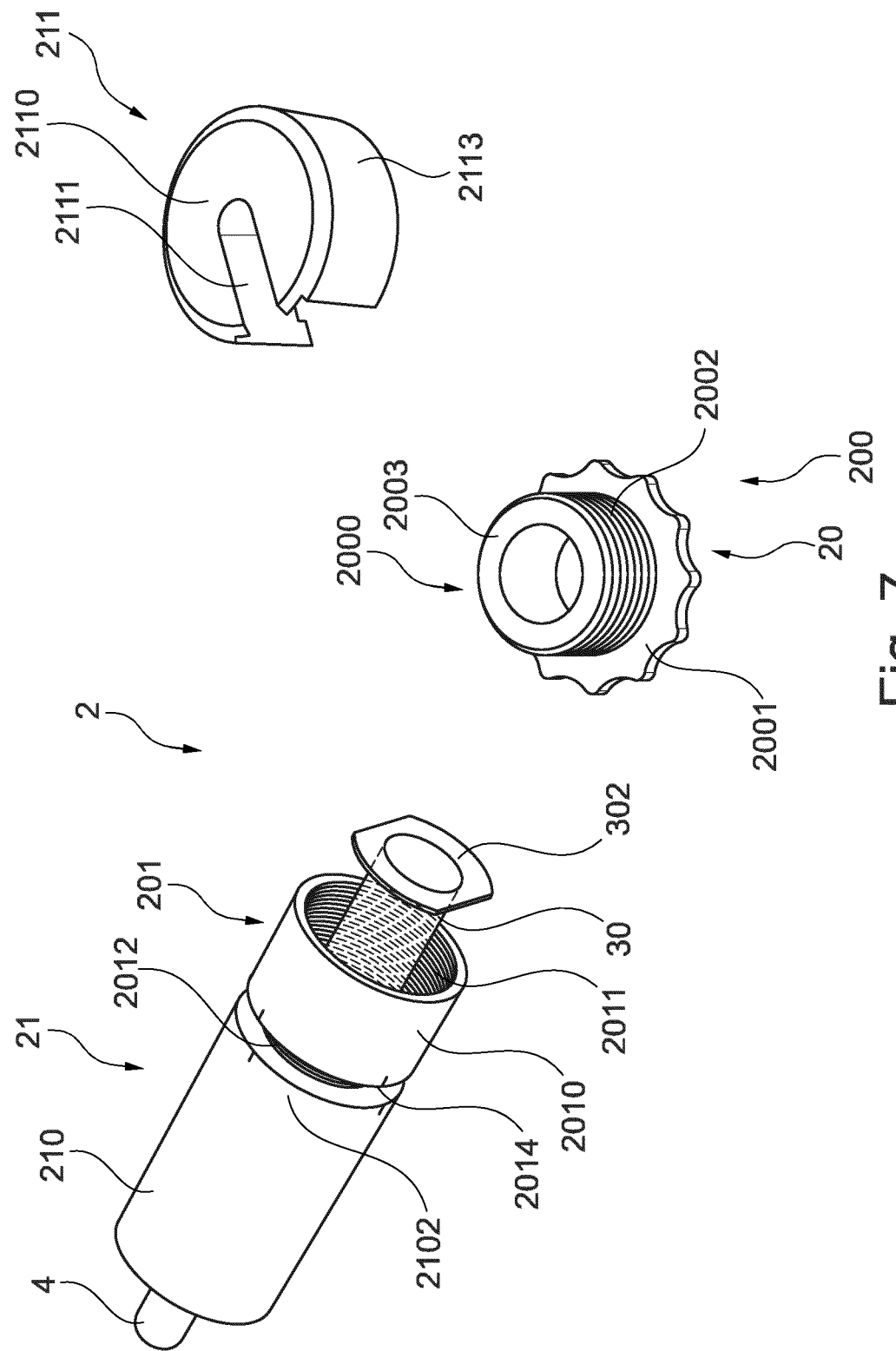
FIG. 7: shows a perspective view of the first embodiment of the displacement device in a partially assembled state as a graphical depiction.
Figure 8:
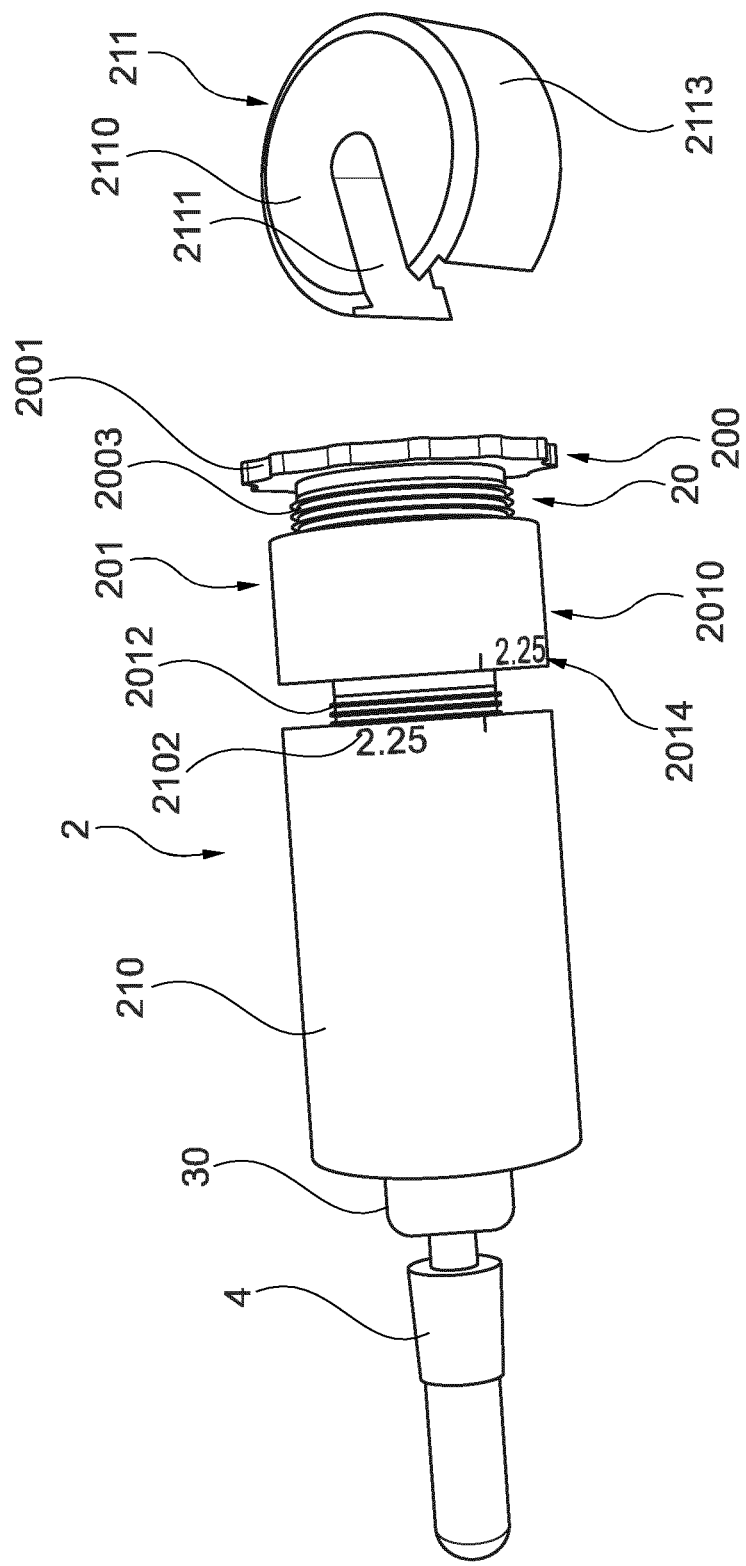
FIG. 8: shows a perspective view of the first embodiment of the displacement device in a further partially assembled state as a graphical depiction.

As can be derived from FIGS. 5a and 5b, the DD 2 comprises a HU 20 and a DU 21. The HU 20 comprises a clamping element 200 and a receiving cylinder 201. The clamping element 200 has a cylindrical body 2000. On the proximal end, the clamping element 200 has a protrusion in the direction perpendicular to the opening direction, OD, in the shape of a toothed ring 2001. Distal to the toothed ring 2001 the cylindrical body of the clamping element 200 has an outer thread 2002. The distal end of the clamping element 200 is a clamping surface 2003, which is perpendicular to the axis of the clamping element 200. The receiving cylinder 201 has at its proximal end an expanded section 2010. In the expanded section 2010 an inner thread 2011 is provided. The inner thread 2011 of the receiving cylinder matches the outer thread 2002 of the clamping element. In the distal section an outer thread 2012 is provided. The transition from the expanded section 2010 to the section with the outer thread 2012 forms an inner proximal surface, which can be referred to as counter surface 2013. As can be derived from FIG. 7, a scale marking 2014 is provided on the outside of the expanded section 2010 at the distal end.

The DU 21 comprises a DC 210 having a distal end section 2100. On the inner surface of the distal end section 2100 an inner thread 2101 is provided. On the outside of the DC 210 at the proximal end a scale marking 2102 is provided. The scale marking 2102 matches the scale marking 2014.

The receiving cylinder 201 and the DC 210 comprise complementarily formed threads 2012, 2101 engaging with each other, which are configured such that a rotation of the DC 210 relative to the receiving cylinder 201 or vice versa results in a linear travel of the DC 210 relative to the receiving cylinder 201 in the OD.

The lift of the threads 2012, 2101 may be in the range of from 0.01 mm to 10 mm, more preferably of from 0.1 mm to 8 mm, even more preferably of from 0.2 mm to 8 mm.

Alternatively, the lift may be in the range from 0.1 mm to 5 mm, more preferably from 0.2 to 4 mm, even more preferably from 0.2 to 3 mm, especially from 0.2 to 2 mm.

In a further alternative, the lift may be in the range from 0.5 mm to 10 mm, more preferably from 0.75 to 8 mm, even more preferably from 1 to 6 mm.

In a specific embodiment the lift may be 1 mm.

The lift denotes the rise, that is as the linear travel the DC 210 performs per revolution about 360° relative to the receiving cylinder 201.

The DD 2 further comprises a TP 211. The TP 211 has a ring body 2110. A slot 2111 is provided in the TP 211. The TP has a ring body 2110 with an inner opening as can be seen best in FIG. 9a. At the distal end of the inner opening a collar 2114 extends inwardly. At the proximal end of the ring body 2110 a PAP 2113 extends in the proximal direction. Between the inner diameter of the PAP 2113 and the inner opening of the ring body 2110 a ST 2112 is thus formed. The thickness of the collar 2114 in the axial direction is smaller than the thickness of the ring body 2110. Thereby a ST2 2115 is formed at the proximal side of the collar 2114.

The dimension of the DD 2 and of its components are adapted and chosen according to the dimensions of the syringe 3 and the SCS 4.

The DD 2 together with the syringe 3 is assembled in the order shown in FIGS. 6, 7, 8 and 9.

Figure 10A:
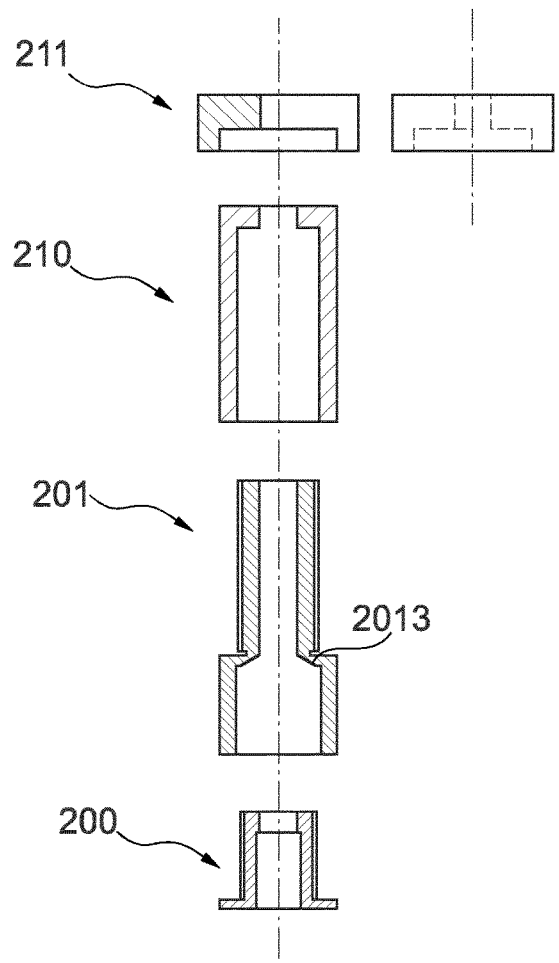
FIG. 10a: shows a sectional view of a second embodiment of the displacement device in a disassembled state.
Figure 10B:
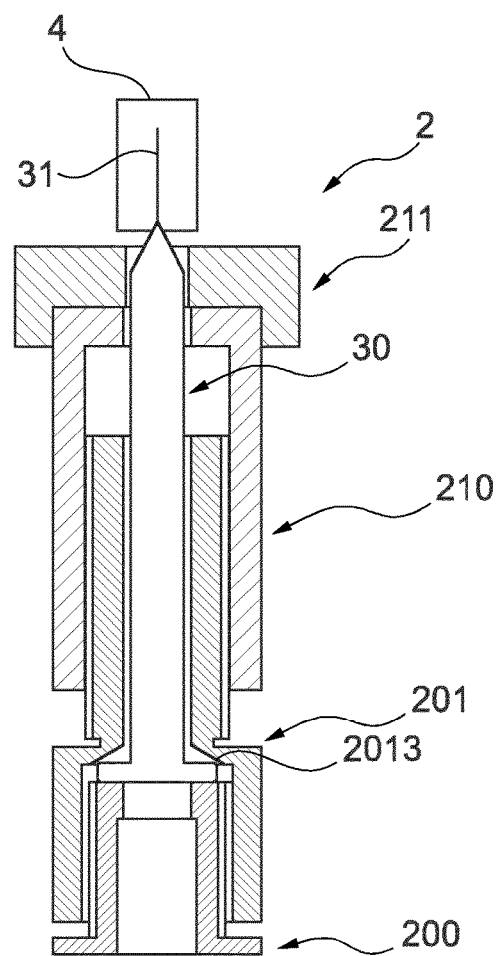
FIG. 10b: shows a sectional view of the second embodiment of the displacement device in an assembled state.
Figure 11A:
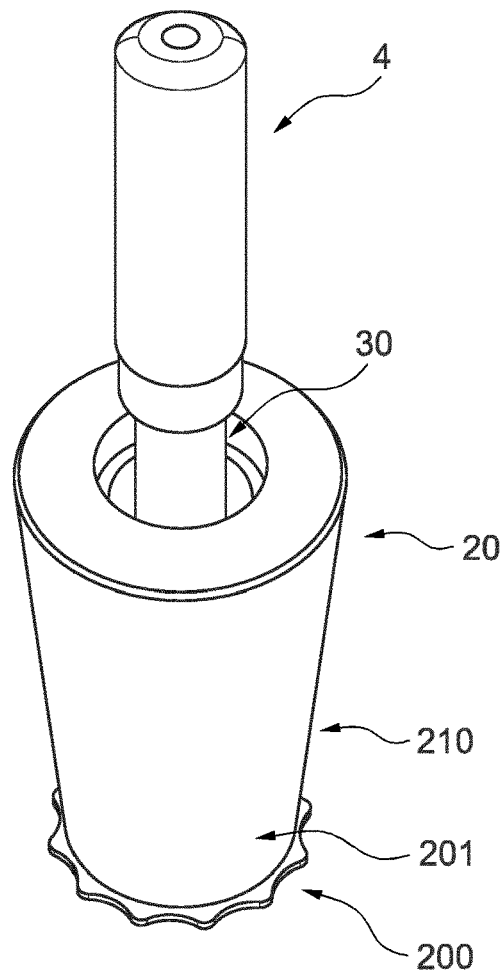
FIG. 11a: shows a perspective view of the second embodiment of the displacement device in an assembled state as a graphical depiction.
Figure 11B:
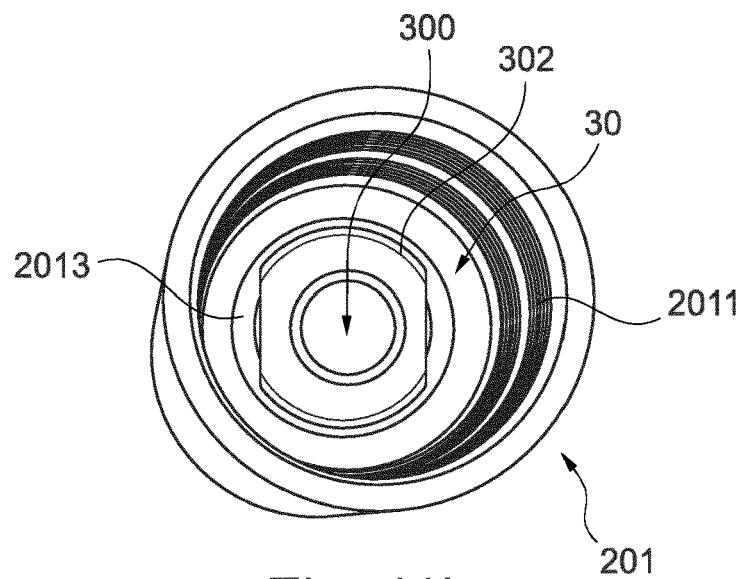
FIG. 11b: shows a perspective view into the proximal end of the receiving cylinder with the syringe inserted into the receiving cylinder as a graphical depiction.

FIGS. 10 and 11 show a second embodiment of the DD 2. This embodiment differs from the first embodiment in that, the counter surface 2003 is tilted and that the TP 211 does not include a collar 2114 and thus no ST2 is formed. The second embodiment is suitable for syringes 3, which are provided with a SCS 4 which has a largest outer diameter which is smaller than the barrel 30 of the syringe 3.

Figure 3:
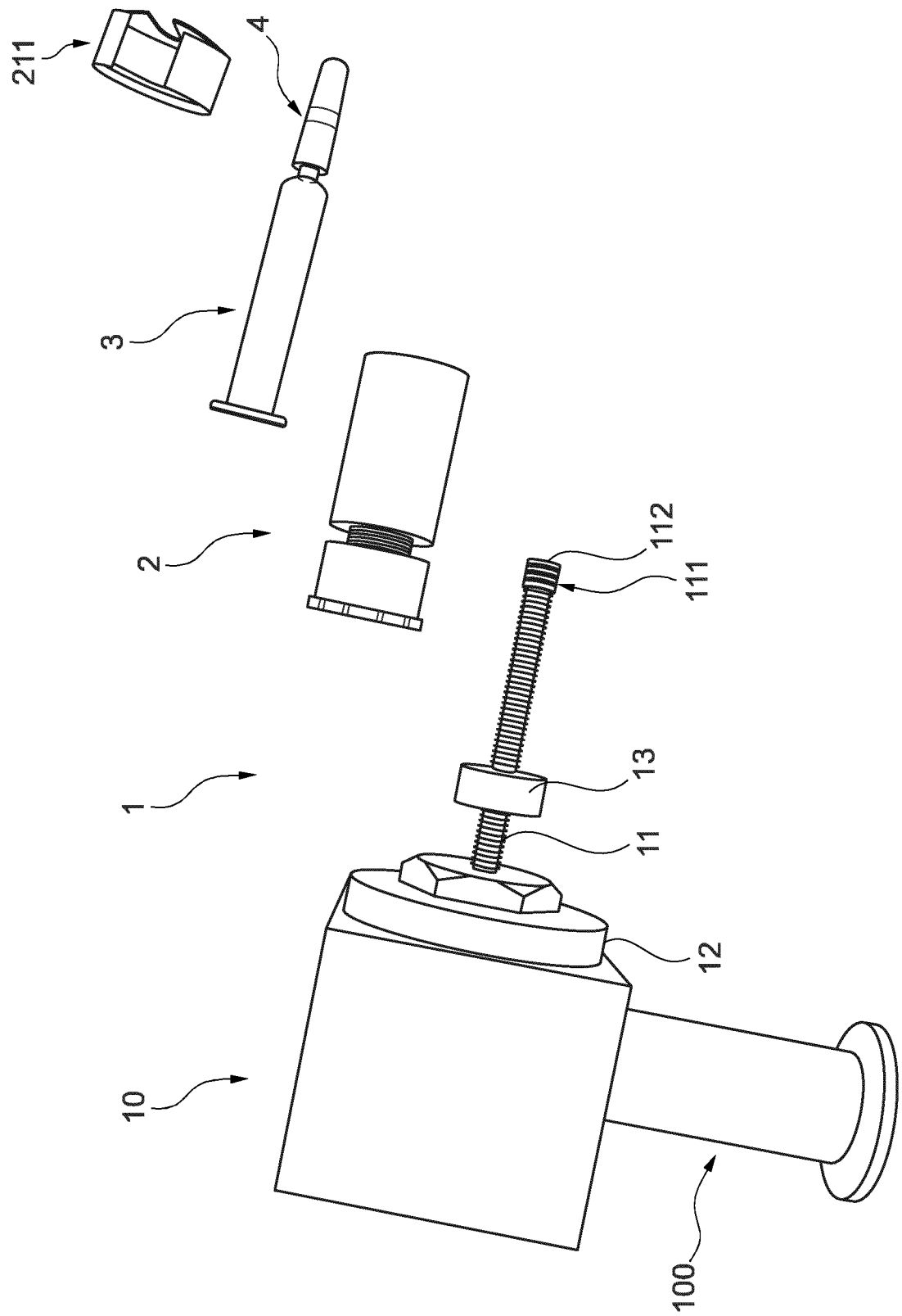
FIG. 3: shows a perspective view of the components of a first embodiment of the testing device according to FIG. 2a in a disassembled state as a graphical depiction.
Figure 4A:
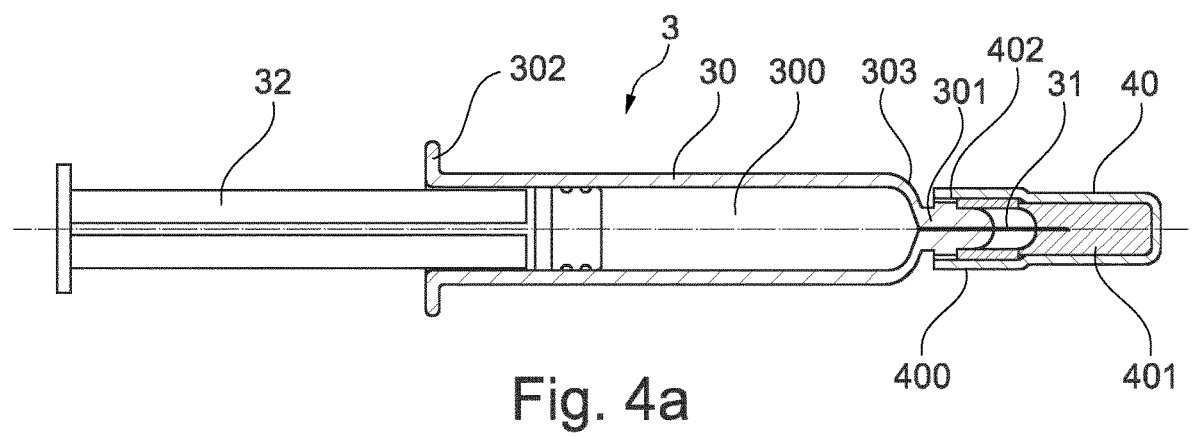
FIG. 4a: shows a schematic sectional view of an embodiment of a syringe with an NS wherein the outer diameter of the barrel is larger the outer diameter of the NS.
Figure 4B:
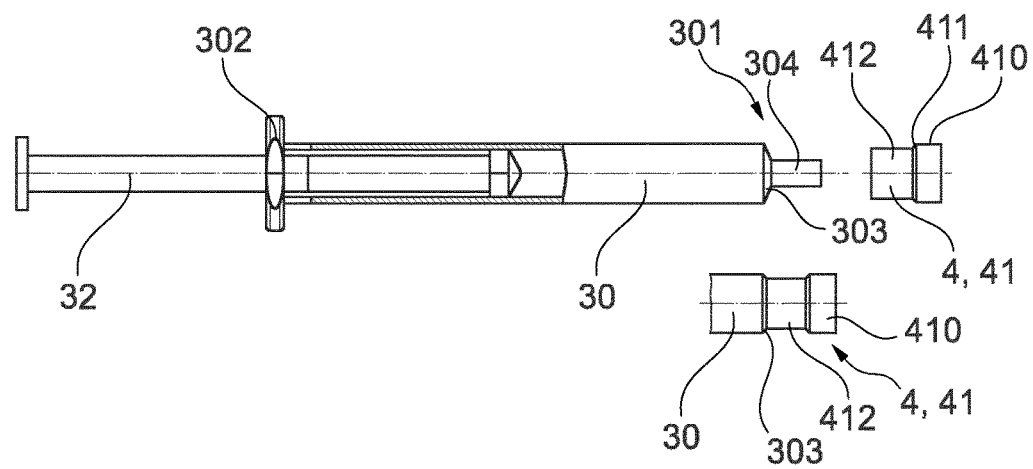
FIG. 4b: shows a schematic sectional view of an embodiment of a syringe with a TIC wherein the outer diameter of the barrel is larger the outer diameter of the TIC.
Figure 9A:
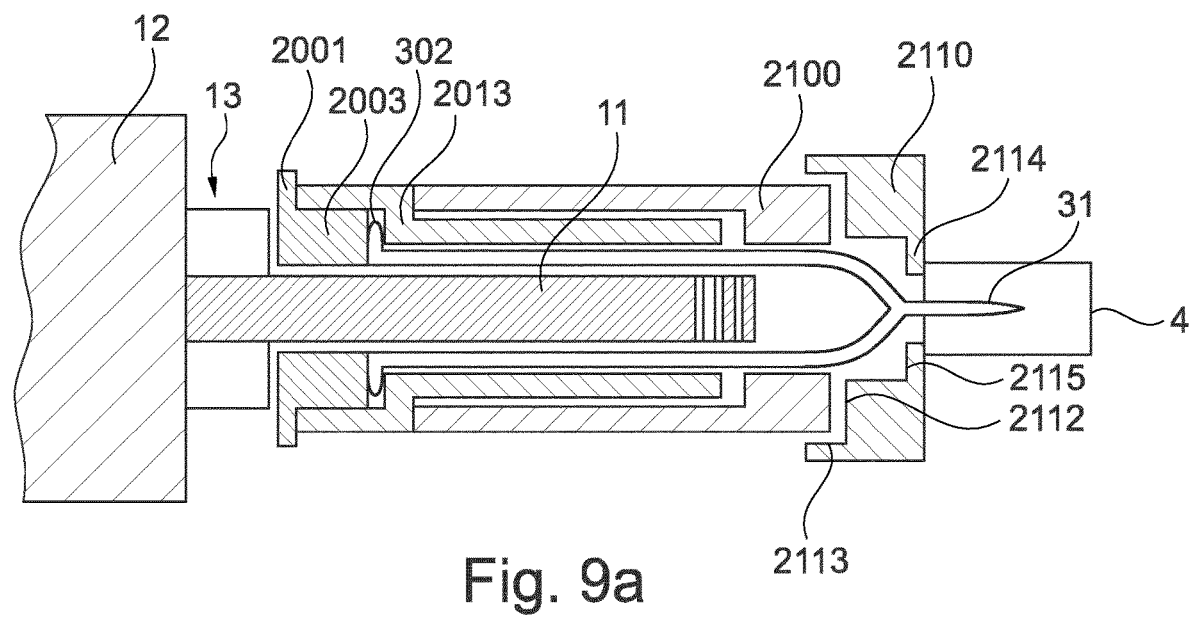
FIG. 9a: shows a sectional view of the first embodiment of the displacement device in an assembled state.
Figure 9B:
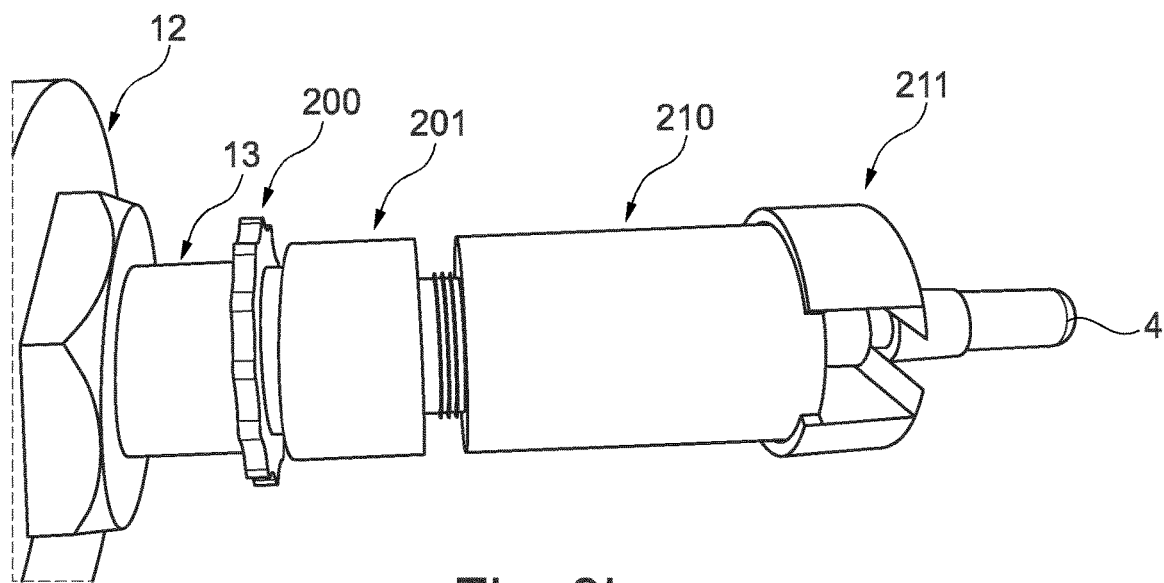
FIG. 9b: shows a perspective view of the first embodiment of the displacement device in an assembled state as a graphical depiction.

With the DD 2 assembled as shown in FIG. 9 or FIG. 10, respectively, the connection of the NS 40 with the syringe 3 can be tested. The DD 2 is placed on the TD 1 by inserting the IP 11 through the clamping element 200 into the lumen 300 of the barrel 30 of the syringe 3 (see FIGS. 3 and 9a).

FIG. 9a shows the DD in the initial position. In this position, the TP 211 abuts with the proximal end of the NS 40 but does not apply a force onto the NS 40 in the OD. By rotating DC 210, the NS 40 will be moved by the TP 211 in the OD. Thereby any sealing between the interior of the syringe 3 and the exterior is compromised, such as between the NC 31 and the NS 40, in particular, for example between the NC 31 and the filling 401 or between the inner surface of the distal end of the NS 40 and the neck 301 of the barrel 30. This can be detected by the detection unit as testing medium can enter the NC 31 and thereby the lumen 300 of the syringe 3 and can reach the detection unit through the channel 110 of the IP 11 and the channel 100 of the body 10 of the TD 1.

EXAMPLES

Material & Methods
Syringes and Components
5 glass syringes and 1 polymeric syringe featuring a staked-in needle cannula and a NS were used (Table 1).

TABLE 1

Syringe configurations used

| Sample | Manufacturer of syringe | Volume of syringe | Material of barrel of syringe | Manufacturer of NS |
|---|---|---|---|---|
| S1 | A | 1 mL | Glass | D |
| S2 | A | 2.25 mL | Glass | D |
| S3 | B | 1 mL | Glass | B |
| S4 | C | 1 mL | Glass | D |
| S5 | C | 2.25 mL | Glass | D |
| S6 | A | 1 mL | COP | D |

Helium Leak CCIT
To analyse the CCI of syringes in a method according to the invention, a channel 100 of a body 10 of a TD 1 as shown in FIG. 2 was mounted on an air tight flange of an ASM340 mass spectrometric helium leak detector (Pfeifer Vacuum, Asslar, Germany). Helium Leak CCI was measured by fixing the inside of the barrel of the syringe held in a DD on the IP of the TD as shown in FIG. 1b. A TC was attached to the protrusion 12 of the body and helium gas was applied into TC, resulting in a saturated helium atmosphere 95% He) in the TC.

According to the US Pharmacopeia, a PFS was considered as tight below the cut-off value of $6*10^{-6}$ mbar l/s (USP 2014<1207>, Package Integrity Evaluation—Sterile Products. pp 1700-1707). Accordingly, this flow rate was used as threshold.

CCIT of a Glass and a Polymeric Syringe at Different Time Points of Measurement

A time series of helium leak measurement was performed over 12 min to investigate a possible impact of gas permeability of polymer syringes versus glass syringes on measured helium leak rates without movement of the SCS.

Figure 12:
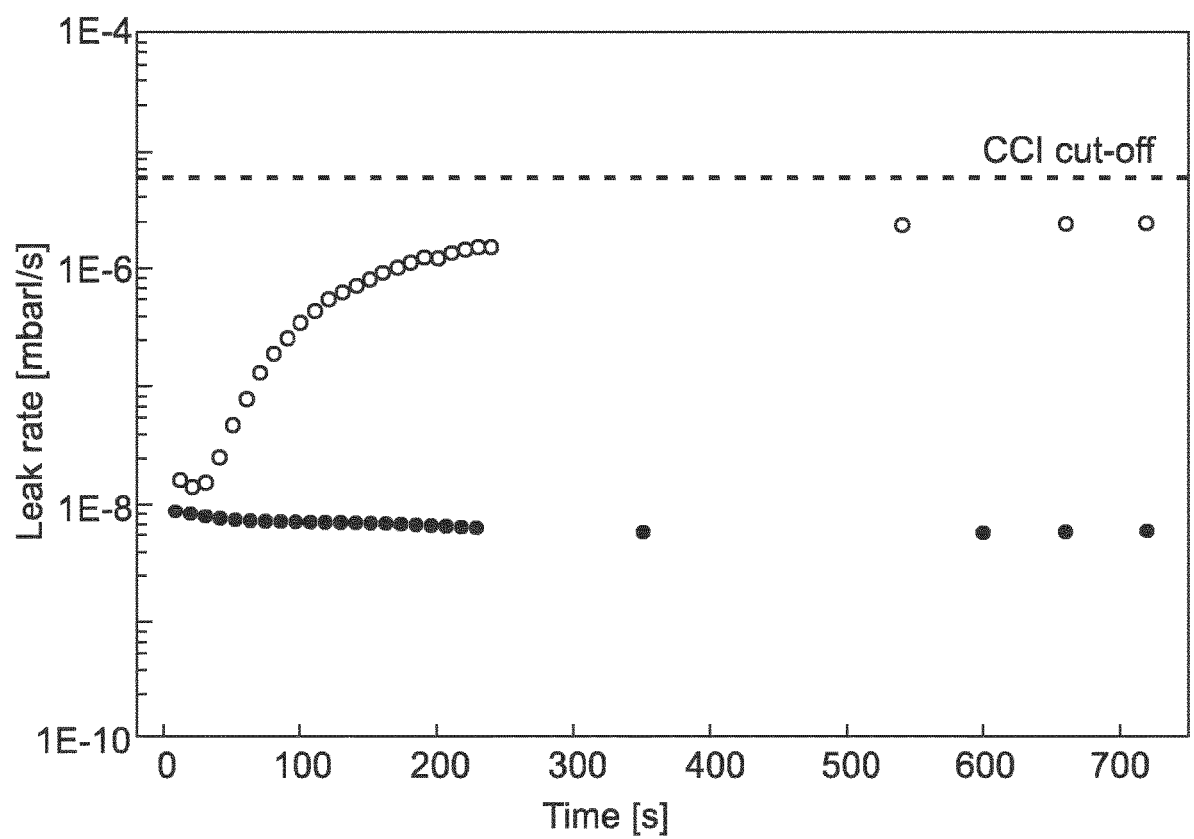
FIG. 12: Inherent Helium leak rates of a glass syringe S2 (solid circles) and an intact polymeric syringe S6 (open circles) over time (12 minutes) without SCS movement.

A glass syringe showed a negligible decrease in the detected He-flow rate over the observed time period from $8.5\times10^{-9}$ mbar*L/s after 10 seconds to $5.7\times10^{-9}$ mbar*L/s after 12 minutes, which is associated to vacuum build up (see FIG. 12).

In contrast, a polymeric syringe showed an inherent increase in helium leak rates starting after about 30 seconds (see FIG. 12). The increase of helium leak rates can for example be explained by diffusion of helium gas through the polymer barrel of the PFS. However, the leak rates of the polymeric syringe stayed well below the CCI threshold defined above.

Assessment of Tip Cap Sensitivity

Assessment of acceptable tip cap movement without compromising CCI was determined by using a TD according to the invention. The maximum acceptable SCS movement was obtained by step wise separating the SCS from the syringe neck according to the method of the invention. The SCS movement rate was 0.2 mm per movement of the DC in the opening direction relative to the receiving cylinder. The maximum acceptable SCS movement was then determined at the TD by measuring the distance with a digital caliper between the initial SCS position and the position at which CCI was compromised, that is at which the threshold value was reached. This distance can as well be calculated from the cumulative angular movement of the DC relative to the receiving cylinder by using the scales on the DC and the receiving cylinders and the lift of the threads of 1 mm.

Figure 13:
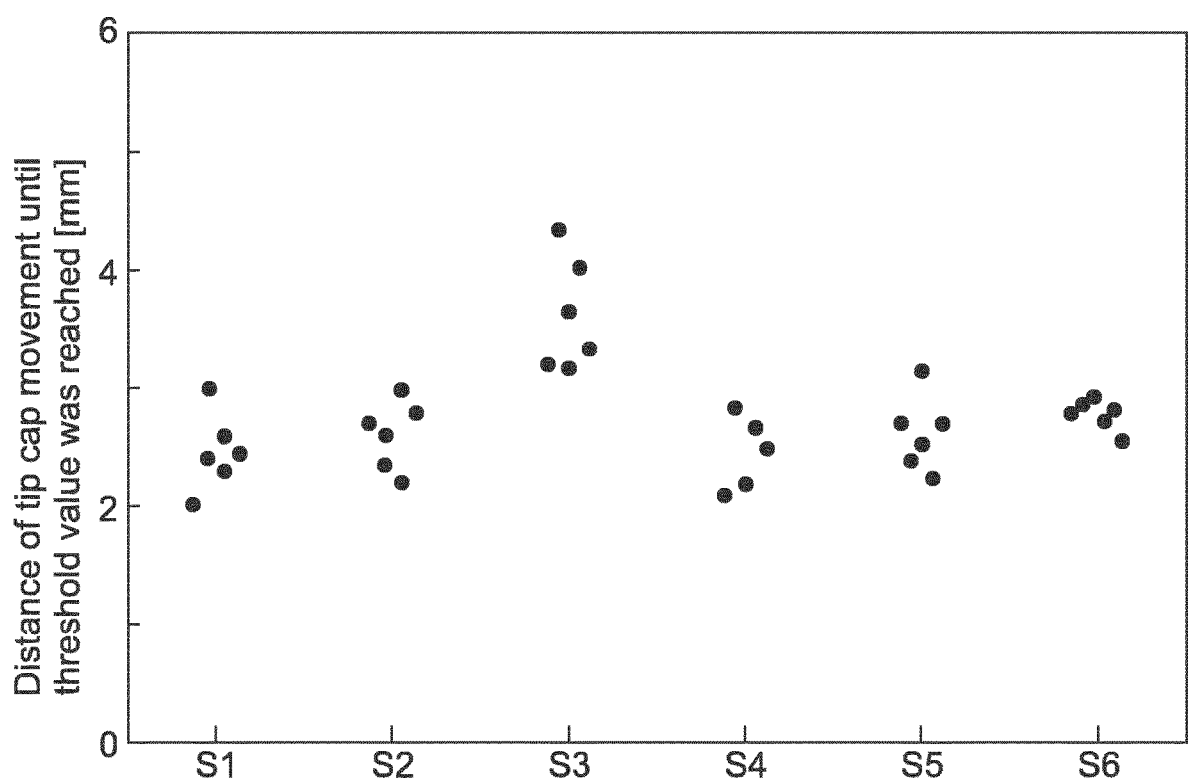
FIG. 13: Determination of SCS movement of 6 PFS (n=6) without compromising CCI.

The results are shown in FIG. 13. SCSs of all tested syringes could be moved for at least 1.7 mm. All tested syringes featuring different syringe barrel/SCS combination showed SCS movement between 1.74 mm and 4.34 mm, until the threshold value was reached, and showed only small variations.

The figure also shows that the method produces reproducible results for identical SCS and syringe combinations. As such the method is suitable for quality control.

LIST OF REFERENCE NUMERALS

1 testing device
10 body
100 channel
11 insertion pipe
110 channel
111 Sealing head
112 sealing ring
12 protrusion
13 distance piece
14 test chamber
140 outlet
141 inlet 142 attachment element
2 displacement device
20 holding unit
200 clamping element
2000 cylindrical body
2001 toothed ring
2002 outer thread
2003 clamping surface
201 receiving cylinder
2010 expanded section
2011 inner thread
2012 outer thread
2013 counter surface
2014 marker
21 displacement unit
210 displacement cylinder
2100 distal end section
2101 inner thread
2102 marker
211 transmission piece
2110 ring body
2111 slot
2112 ST
2113 PAP
2114 collar
2115 ST2
3 syringe
30 barrel
300 lumen
301 neck of the barrel
302 flange
303 shoulder
304 Luer cone
31 needle cannula
32 plunger
4 SCS
40 NS
400 rigid cover
401 filling
402 sealing means
410 TIC
410 expanded end section
411 Step
412 proximal section

The invention claimed is:

1. A displacement device for providing a displacement of a syringe closure system, SCS, which closes a distal end of the syringe from outside of the syringe, relative to the syringe in an opening direction, a proximal end of the syringe having a flange, comprising:
a holding unit, HU, for holding at least part of the syringe and
a displacement unit, DU, which is movably attached to the holding unit for movement by a predetermined distance in the opening direction, wherein the holding unit comprises:
a receiving cylinder for receiving at least part of the barrel of the syringe and
a clamping element for clamping at least part of the flange of the syringe between the clamping element and the receiving cylinder, wherein a distal end of the clamping element comprises a clamping surface for contact with a proximal surface of the flange; and
wherein the DU comprises a displacement cylinder, DC, movably attached to a portion of the receiving cylinder distal to the flange by a screw type connection.

2. The displacement device according to claim 1, wherein the receiving cylinder and the clamping element are connected by a screw type connection.

3. The displacement device according to claim 1, wherein a proximal inner surface of the receiving cylinder acts as counter surface to the clamping surface.

4. The displacement device according to claim 3, wherein the proximal inner surface is perpendicular to the axis of the receiving cylinder or wherein the proximal inner surface is tilted to the axis of the receiving cylinder.

5. The displacement device according to claim 1, wherein the smallest inner diameter of the receiving cylinder is larger than or equal to the outer diameter of the barrel of the syringe but smaller than the outer diameter of the flange of the syringe to be held in the displacement device.

6. The displacement device according to claim 1, wherein the DU comprises a transmission piece, TP, for transmitting axial movement from the DC to the SCS in the opening direction.

7. The displacement device according to claim 6, wherein the TP has the shape of a ring body with a proximal annular protrusion, PAP, along the outer circumference of the ring body.

8. The displacement device according to claim 6, wherein the outer diameter of the TP is larger than the outer diameter of the DC.

9. The displacement device according to claim 6, wherein the TP has an inner opening and the inner diameter of the inner opening is equal to or larger than the outer diameter of the barrel of the syringe which is to be held in the displacement device and the inner diameter of the inner opening or of a collar provided on the inner opening is smaller than the largest diameter of the SCS.

10. The displacement device according to claim 6, wherein the TP has a slot with a direction perpendicular to the axis of TP at a distal end extending from the inner diameter of the inner opening or of a collar to the outer diameter of the TP over the entire radius of the TP, wherein the slot is open at its peripheral end and extends axially over the entire TP.

11. The displacement device according to claim 10, wherein the width of the slot and the inner diameter of the inner opening or the inner diameter of the collar correspond to or are larger than the neck of the barrel of the syringe.

12. The displacement device according to claim 6, wherein at least a distal end of the DC has a friction reducing coating and/or at least a proximal surface of the TP has a friction reducing coating.

13. The displacement device according to claim 6, wherein the TP has a circumferential ball bearing, this circumferential ball bearing being in a plane perpendicular to the axis of the TP.

14. The displacement device according to claim 1, wherein at least one scale marking is provided on at least part of the outer circumference of the DC and on the outer circumference of the receiving cylinder.

15. A testing device, TD, for leakage testing of a connection of a SCS for a syringe with the syringe, wherein the testing device comprises a displacement device according to claim 1.

16. The testing device according to claim 15, wherein the TD comprises an insertion pipe, IP, for insertion into the barrel of the syringe, in particular into the lumen of the barrel and wherein the IP has a channel extending through the IP for providing fluid connection between the lumen of the barrel of the syringe and a detection unit.

17. The testing device according to claim 15, wherein the TD comprises a distance piece, DP, movably attached to the IP for setting and holding a distance between the distal end of the IP and the distal end of the lumen of the barrel of the syringe.

18. The testing device according to claim 17, wherein the clamping element has a proximal annular extension, PAE, and the outer diameter of the DP, is equal to or smaller than the inner diameter of the PAE of the clamping element.

19. The testing device according to claim 16, wherein the IP has at least one sealing ring arranged at the outer circumference of a distal end of the IP, preferably on a sealing head which is screwed onto the distal end of the IP.

20. The testing device according to claim 15, wherein the TD comprises a test chamber, TC, detachably connected a body of the TD, and the TC comprises an inlet for input of a testing medium.

21. A method for leakage testing of a connection of a SCS for a syringe with the syringe, wherein the method is carried out with a testing device according to claim 15 with a displacement device, wherein the displacement device provides a displacement of the syringe closure system, SCS, which closes the distal end of the syringe from outside of the syringe, relative to the syringe in an opening direction, comprising:
 a holding unit, HU, for holding at least part of the syringe and
 a displacement unit, DU, which is movably attached to the holding unit for movement by a predetermined distance in the opening direction, wherein the holding unit comprises:
 a receiving cylinder for receiving at least part of the barrel of the syringe and
 a clamping element for clamping at least part of the flange of the syringe between the clamping element and the receiving cylinder;
 and wherein the DU comprises a displacement cylinder, DC, movably attached to the receiving cylinder by a screw type connection.

22. The method according to claim 21, wherein the method comprises the steps of:
 a) placing a syringe with a SCS in a DD,
 b) placing the DD on a TD,
 c) placing a TC over the DD,
 d) evacuating a part of the lumen of the syringe,
 e) exposing the syringe to testing medium, and
 f) measuring the amount of testing medium at a detection unit of the TD, which has passed through any leakage between the SCS and the syringe.

23. The method according to claim 22, wherein step a) comprises the steps of:
 a1) inserting the receiving cylinder into the DC,
 a2) inserting the syringe with the SCS from the proximal end of the receiving cylinder into the receiving cylinder,
 a3) clamping the flange of the syringe barrel to the receiving cylinder, and
 a4) attaching the TP to the distal end of the DC.

24. The method according to claim 22, wherein step a) comprises a step a5) of
 positioning the TP into an initial position, wherein the TP abuts to the proximal end of the largest diameter of the SCS without applying force to the SCS, by moving the DC relative to the receiving cylinder in the opening direction.

25. The method according to claim 22, wherein step b) comprises the step of:
 b1) inserting an IP of the TD into the lumen of the syringe barrel and
 b2) advancing the IP in the lumen of the barrel of the syringe into the vicinity of the shoulder of the barrel of the syringe and
 b3) moving the DP on the IP to a position, wherein the proximal side of the DD is in contact with the distal side of the DP.

26. The method according to claim 24, wherein step d) is carried out by applying vacuum to the lumen of the barrel via the IP.

27. The method according to claim 22, wherein the method further comprises the step of
 g1) determining whether the measured amount of testing medium which entered the lumen of the barrel exceeds a pre-set threshold value or
 g2) verifying whether the measured amount of testing medium exceeds a pre-set threshold value at a pre-set distance of the SCS from the initial position in the opening direction.

28. The method according to claim 22, wherein the method comprises the step h) of moving the DC in the opening direction by a predetermined distance relative to the receiving cylinder.

29. The method according to claim 28, wherein the method further comprises the steps of
 i) removing the TC before step h) and
 j) placing the TC after step h).

* * * * *